(12) United States Patent
Robinson

(10) Patent No.: US 9,968,380 B2
(45) Date of Patent: May 15, 2018

(54) LAMINOPLASTY METHOD

(71) Applicant: James C. Robinson, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 0 days. days.

(21) Appl. No.: 14/563,883

(22) Filed: Dec. 8, 2014

(65) Prior Publication Data

US 2015/0094771 A1  Apr. 2, 2015

Related U.S. Application Data

(62) Division of application No. 13/655,393, filed on Oct. 18, 2012, now Pat. No. 8,915,947.

(51) Int. Cl.
| | |
|---|---|
| *A61B 17/70* | (2006.01) |
| *A61B 17/88* | (2006.01) |
| *A61B 17/02* | (2006.01) |
| *A61B 17/80* | (2006.01) |
| *A61B 17/34* | (2006.01) |

(52) U.S. Cl.
CPC ...... *A61B 17/7059* (2013.01); *A61B 17/3421* (2013.01); *A61B 17/3468* (2013.01); *A61B 17/7071* (2013.01); *A61B 17/7074* (2013.01); *A61B 17/7076* (2013.01); *A61B 17/808* (2013.01); *A61B 17/8894* (2013.01); *A61B 2017/3443* (2013.01)

(58) Field of Classification Search
CPC . A61B 17/02; A61B 17/0206; A61B 17/0218; A61B 17/0293; A61B 17/3421; A61B 17/3462; A61B 17/3468; A61B 17/7062; A61B 17/7064; A61B 17/7065; A61B 17/7068; A61B 17/7071; A61B 2017/0256; A61B 2017/3443; A61B 2017/3445; A61B 2017/3447; A61B 1/32; A61F 2/4405; A61F 2/4611
See application file for complete search history.

(56) References Cited

U.S. PATENT DOCUMENTS

| | | | |
|---|---|---|---|
| 4,929,247 | A | 5/1990 | Rayhack |
| 5,928,139 | A | 7/1999 | Koros et al. |
| 6,491,695 | B1 | 12/2002 | Roggenbuck |
| 6,648,895 | B2 | 11/2003 | Burkus et al. |
| 7,264,620 | B2 | 9/2007 | Taylor |
| 8,105,366 | B2 | 1/2012 | Null et al. |
| 8,152,720 | B2 | 4/2012 | Loftus et al. |
| 8,246,682 | B2 | 8/2012 | Slivka et al. |
| 2005/0096507 | A1* | 5/2005 | Prosek ............. A61B 17/34 600/204 |

(Continued)

FOREIGN PATENT DOCUMENTS

| | | |
|---|---|---|
| CN | 1678248 A | 10/2005 |
| CN | 102596074 A | 7/2012 |

(Continued)

*Primary Examiner* — Christian Sevilla
*Assistant Examiner* — Tracy Kamikawa
(74) *Attorney, Agent, or Firm* — FisherBroyles, LLP; Anthony J. DoVale

(57) ABSTRACT

A portal for accessing a desired lamina portion of a desired cervical vertebra to perform a laminoplasty. In one aspect, a laminoplasty portal is presented that defines an interior conduit and has a first sidewall section and a second sidewall section.

10 Claims, 22 Drawing Sheets

(56) References Cited

U.S. PATENT DOCUMENTS

| | | | |
|---|---|---|---|
| 2005/0216002 A1* | 9/2005 | Simonson | A61B 17/0218 606/279 |
| 2006/0195017 A1* | 8/2006 | Shluzas | A61B 17/025 600/210 |
| 2006/0200186 A1 | 9/2006 | Marchek et al. | |
| 2008/0140129 A1 | 6/2008 | Dalton | |
| 2008/0161814 A1 | 7/2008 | McAllister et al. | |
| 2008/0214898 A1 | 9/2008 | Warren | |
| 2010/0030065 A1 | 2/2010 | Farr | |
| 2010/0057127 A1 | 3/2010 | McGuire et al. | |
| 2011/0034777 A1 | 2/2011 | Ames et al. | |
| 2011/0034781 A1* | 2/2011 | Loftus | A61B 17/7076 600/215 |
| 2011/0144766 A1 | 6/2011 | Kale et al. | |
| 2012/0010471 A1* | 1/2012 | Mire | A61M 29/00 600/210 |
| 2012/0158061 A1* | 6/2012 | Koch | A61B 17/3421 606/248 |

FOREIGN PATENT DOCUMENTS

| | | |
|---|---|---|
| KR | 10-0897928 | 5/2009 |
| WO | WO200023013 A1 | 4/2000 |
| WO | WO2009151734 A1 | 12/2009 |
| WO | WO2010/144636 | 12/2010 |

\* cited by examiner

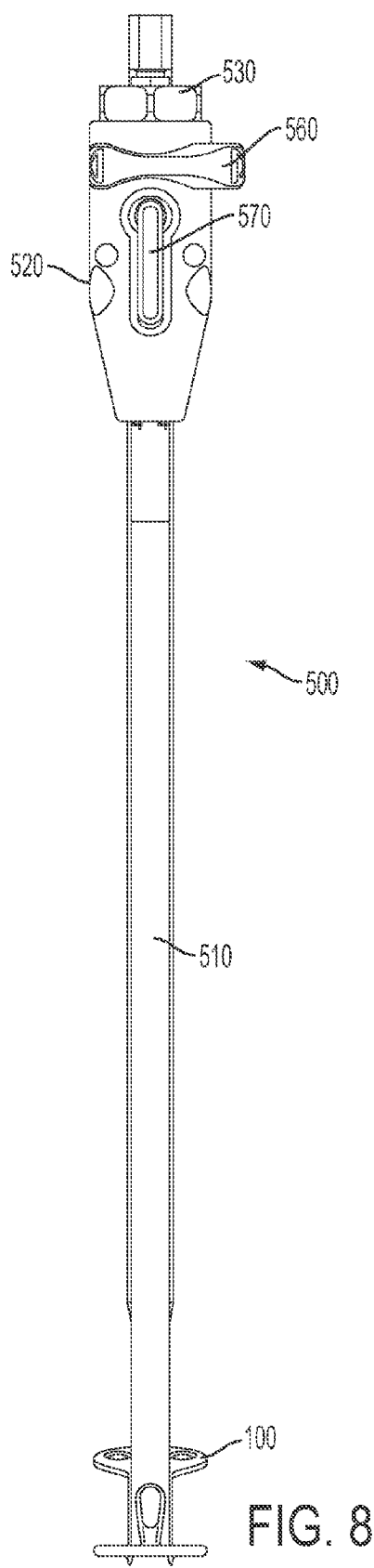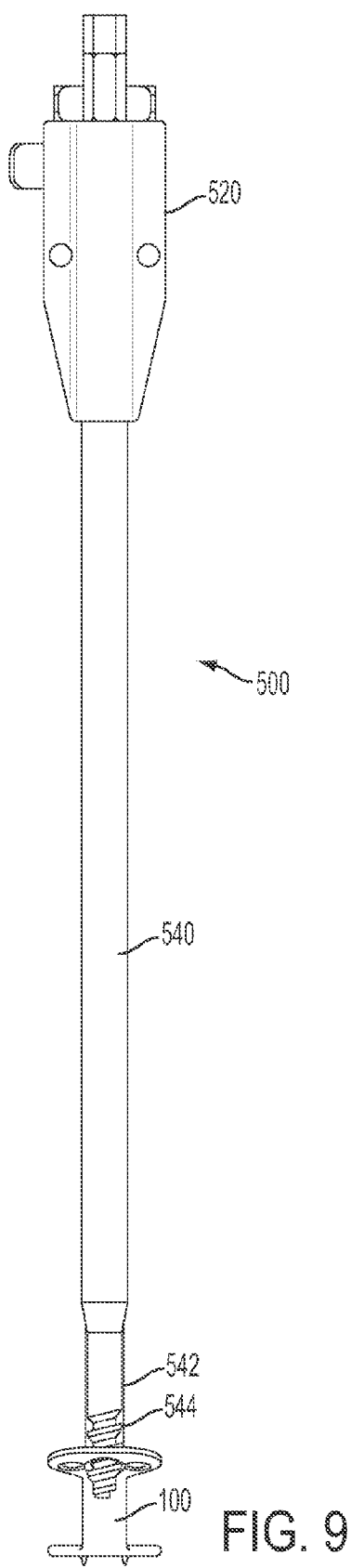

LAMINOPLASTY METHOD

CONTINUITY

This application claims the benefit of, priority to and is a divisional of U.S. application Ser. No. 13/655,393 filed on Oct. 18, 2012, now U.S. Pat. No. 8,915,947, which is incorporated herein in its entirety by reference.

FIELD OF THE INVENTION

The present invention relates generally to surgical procedures, most particularly for use in performing a laminoplasty to treat cervical stenosis in the spine. More specifically, the invention pertains to a method for increasing the area of the spinal canal by securing a separated lamina portion of a desired cervical vertebra in a relief position.

BACKGROUND OF THE INVENTION

Spinal stenosis is a pathology of the spine that involves the narrowing of the spinal canal, through which the spinal cord and nerve roots run. This narrowing may be congenital and, consequently, can affect patients at any age. Spinal stenosis may result from thickening and calcification of spinal ligaments. For example, calcification can result from deposits of calcium salts within the spine. In addition, spinal stenosis can result when bones and joints are enlarged, leading to the formation of osteophytes (bone spurs). A significant cause of osteophytes is spondylosis, in which spinal discs lose water and become less dense. Also, a bulging or herniated disc may place pressure on the spinal cord or nerve root such that the area of the spinal canal is reduced. Finally, diseased bone or tumors can extend into the spinal cord area, decreasing the space available for nerve roots within the spinal canal.

Compression of the spinal cord resulting from spinal stenosis can produce pain, weakness, or loss of feeling in the patient. Additionally, spinal cord compression can lead to myelopathy, which causes neurological damage and results in spinal cord malfunction. If left untreated, the compression can eventually damage the circulatory system within the spinal cord, leading to more severe myelopathy.

Two surgical methods are traditionally used to decompress the spinal cord from a posterior approach to the spine. First, the laminectomy involves the removal of the lamina and spinous processes in order to expose the dura covering the spinal cord. Due to the removal of portions of the supporting structures at the posterior of the vertebra that are used to align the spinal column, a laminectomy can create postural deformities in patients. In addition, there is a risk that the procedure will lead to substantial scar formation in the patient. In order to address these concerns, a graft may be installed between the vertebral bones involved to promote fusion. However, this may lead to a decrease in the range of motion in the spine, and there may also be accelerated degeneration of the vertebrae above and below the repaired vertebra.

The second method traditionally used to decompress the spinal cord is the laminoplasty. In a laminoplasty procedure, the targeted vertebra is cut and the lamina repositioned so that the lamina is lifted off the dura and the spinal canal is thus enlarged. Then, a plate and/or a graft are inserted to permanently enlarge the spinal canal. There are generally two techniques used to perform a laminoplasty. First, the unilateral or "open door" laminoplasty involves cutting entirely through a first portion of the lamina on the first side of midline of the targeted vertebra, while a second portion of the lamina on the second side of midline is only cut partially through to create a hinge. Then, the first lamina portion is hinged away from the spinal cord to increase the size of the spinal canal. Finally, a graft and/or plate is inserted into the opening to permanently enlarge the spinal canal. Second, the bilateral or "French door" laminoplasty involves cutting entirely through the midline of the spinous process, and then cutting partially through both sides of the lamina portion, creating two hinges. The vertebra can then be opened at the bisected spinous process, and a graft or plate can be inserted into the opening to permanently enlarge the spinal canal.

Unlike the laminectomy, the laminoplasty does not involve the excising of any bone material. In addition, when compared to the laminectomy, the laminoplasty may provide greater stability. A wider range of motion for the patient is maintained compared to a fusion. Through the use of laminar fusion and fixation techniques in a laminoplasty procedure, the achieved decompression and position of the displaced lamina can be more effectively maintained.

Despite the advances that have been achieved in laminoplasty procedures, there are still some limitations in the effectiveness of the procedures and the ease with which the procedures are completed, especially when performed on the cervical vertebrae. For example, the present technique requires the surgeon to make a large incision to reach the spine, which includes stripping of muscle and ligament attachments to the bone, and this can lead to significant muscle and tissue damage. In addition, in cervical spine surgeries, the smaller size of the target vertebra makes the operation more complicated. For instance, the surgeon may find it difficult to make precise adjustments within the operating space or to know whether the lamina has been displaced an appropriate distance. Further, in some patients, the increase in area that can be achieved by current techniques is insufficient to provide complete relief from spinal cord compression. Finally, due to the uneven nature of "open door" laminaplasties, patients may have a slight imbalance in their spines following the procedure, and the increase in spinal canal diameter is asymmetric.

Similarly, the laminoplasty plates that are currently used also have limitations. For example, many current laminoplasty plates are too large in size for insertion into small incisions or for effective attachment to cervical vertebrae. In addition, current plates frequently lack the stability required to permanently orient the lamina in an appropriate position. Also, the design of existing laminoplasty plates often makes the process of attaching the plate to the vertebra and lamina very challenging. Finally, many existing laminoplasty plates are not adequately constructed to allow for conjunctive use of bone fusion material. Existing plates are also cumbersome for use with less invasive surgical procedures.

Accordingly, it remains desirable in the pertinent art to provide laminoplasty plates to address the limitations associated with known plates, including but not limited to those limitations discussed above. Additionally, it is desirable in the pertinent art to provide methods and systems for using the said laminoplasty plates to address the limitations associated with known methods and systems, including but not limited to those limitations discussed above.

SUMMARY

Presented herein is a laminoplasty system comprising a laminoplasty plate, a lamina setting tool, and a laminoplasty portal. In one aspect, the laminoplasty plate comprises a proximal end portion having a bottom surface defined in a first plane and a distal end portion having a bottom surface defined in a second plane.

In one aspect, a lamina setting tool is presented for positioning the lamina portion of the desired cervical vertebra in the relief position. In one aspect, the tool comprises a rotatable threaded shaft comprising an adjustable stop and a guide having a body portion and a first support arm. In this aspect, the body portion has a fixed length and is spaced therefrom the rotatable threaded shaft. The guide is coupled to the rotatable threaded shaft by the first support arm, which is connected to the body portion. At the distal end of the first support arm, the guide is coupled to the rotatable threaded shaft. In this aspect, the stop is selectively adjustable to correspond to a given limited depth, which will prevent over penetration of the threaded member through the underside of the lamina into the spinal canal.

In another aspect, the lamina portion is controllably elevated to a relief position in which the spinal canal of the desired cervical vertebra has a relief cross-sectional area that is greater than the pre-operative cross-sectional area, wherein the lamina portion is subsequently secured in an elevated position.

In a further aspect, the lamina setting tool can be provided to assist with the step of controllably raising and securing the lamina portion in the relief position. In this aspect, the guide is configured to detachably mount to the mountable portion of the laminoplasty plate.

When using the lamina setting tool with a standard portal, the portal must raise with the lamina, which can permit fluid and soft tissue to obstruct visualization and/or mechanically interfere with the procedure. Therefore, in one exemplified aspect, the laminoplasty portal is provided and comprises a substantially enclosed conduit defining an interior channel and a circumferential sidewall. In one aspect, the circumferential sidewall comprises a first sidewall section and an opposed second sidewall section, where the first sidewall section and second sidewall section are configured to slide longitudinally with respect to one another. In this fashion, in a first position, the distal ends of the two sidewall sections are substantially coextensive against the first and second lamina portions. As the first lamina portion is raised, the distal end of the first sidewall section raises along with it to a second position, leaving the distal end of the second sidewall section substantially adjacent the first lateral mass portion.

Related methods of operation are also provided. Other apparatuses, methods, systems, features, and advantages of the laminoplasty plates and the method of their use will be or become apparent to one with skill in the art upon examination of the following figures and detailed description. It is intended that all such additional apparatuses, methods, systems, features, and advantages be included within this description, be within the scope of the laminoplasty plates and the method of their use, and be protected by the accompanying claims.

DESCRIPTION OF THE FIGURES

FIG. 8 is a back side elevational view of the lamina setting tool of FIG. 7.

FIG. 9 is a front side elevational view of the lamina setting tool of FIG. 7.

DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Figure 1:
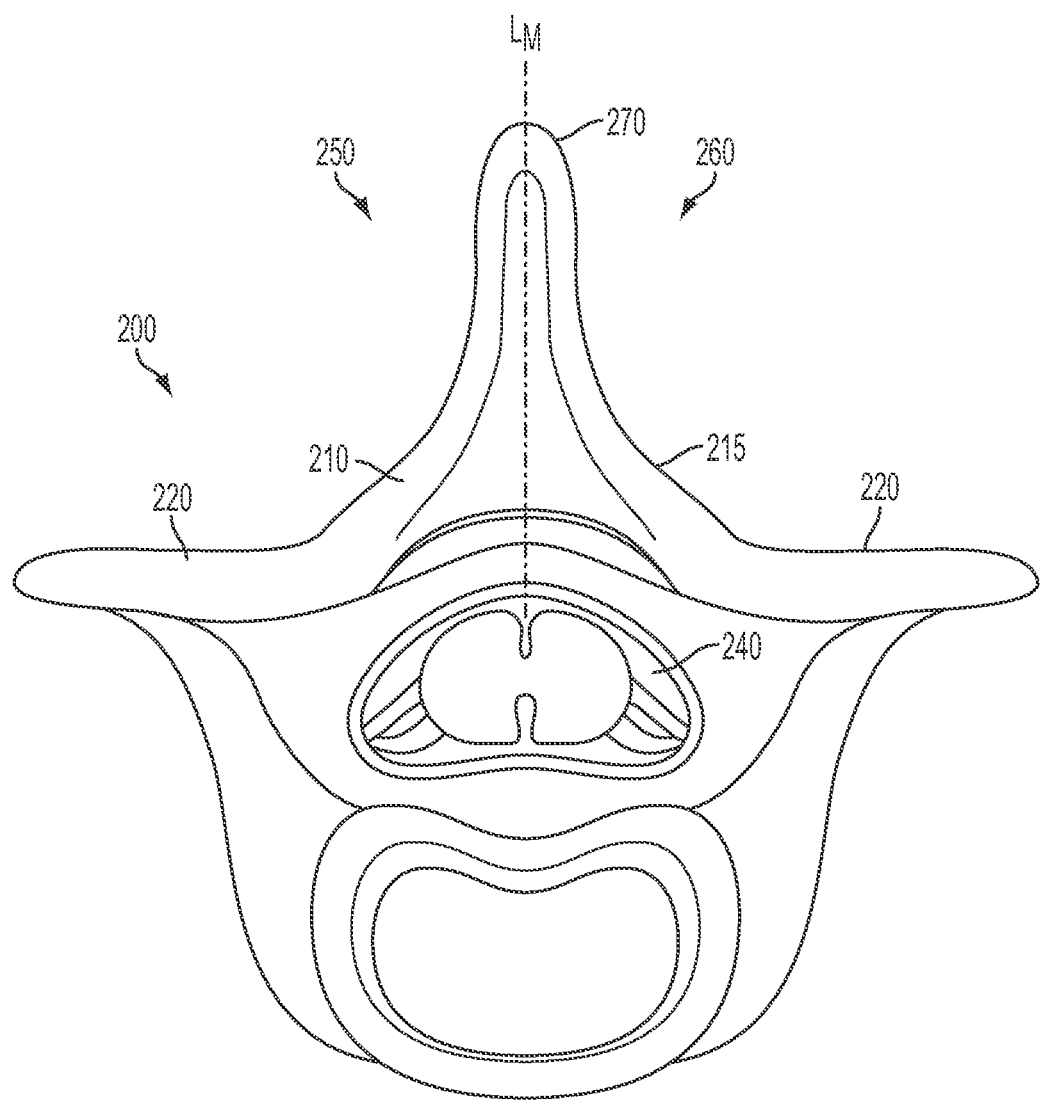
FIG. 1 is top plan view of an exemplified cervical vertebra showing the spinal canal having a pre-operative cross-sectional area.
Figure 2:
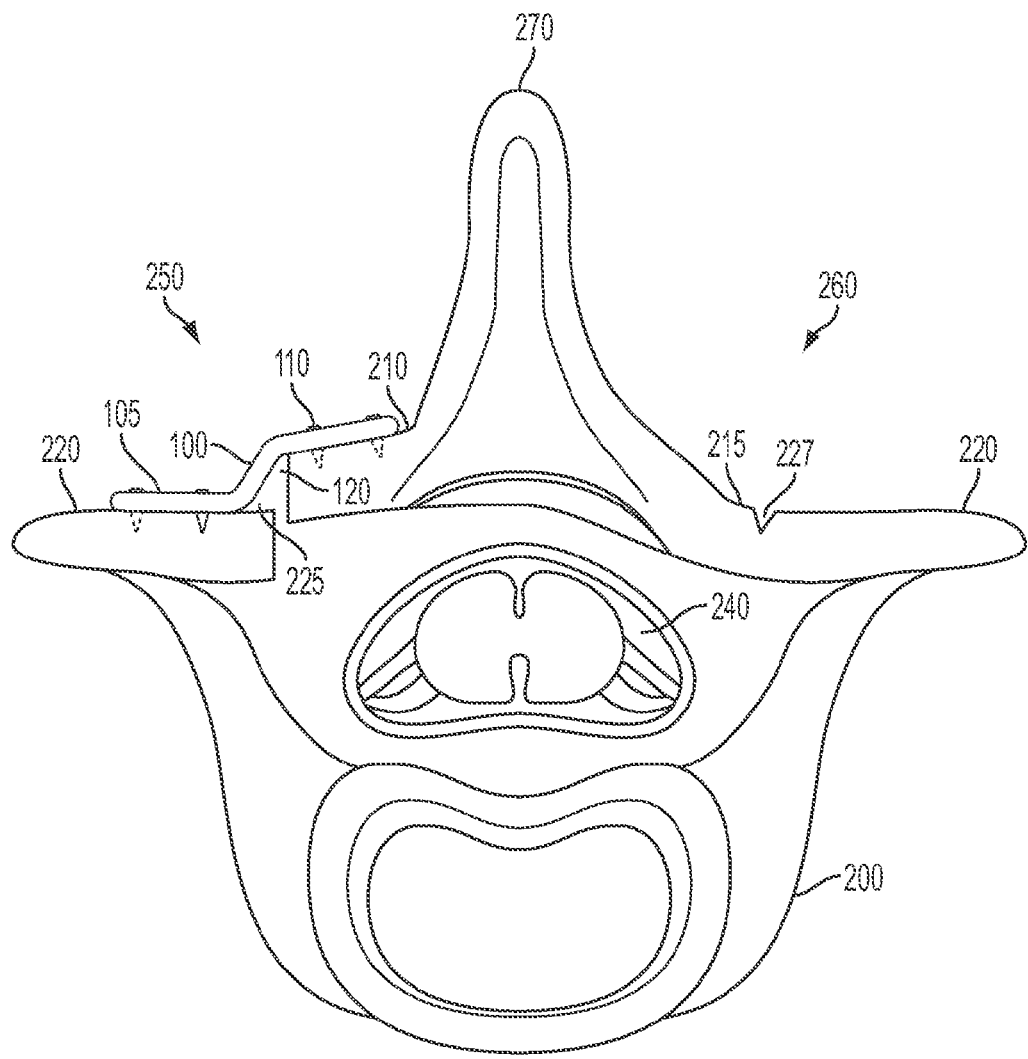
FIG. 2 is a top plan view of the cervical vertebra of FIG. 1, showing a first lamina portion in the relief position.
Figure 3:
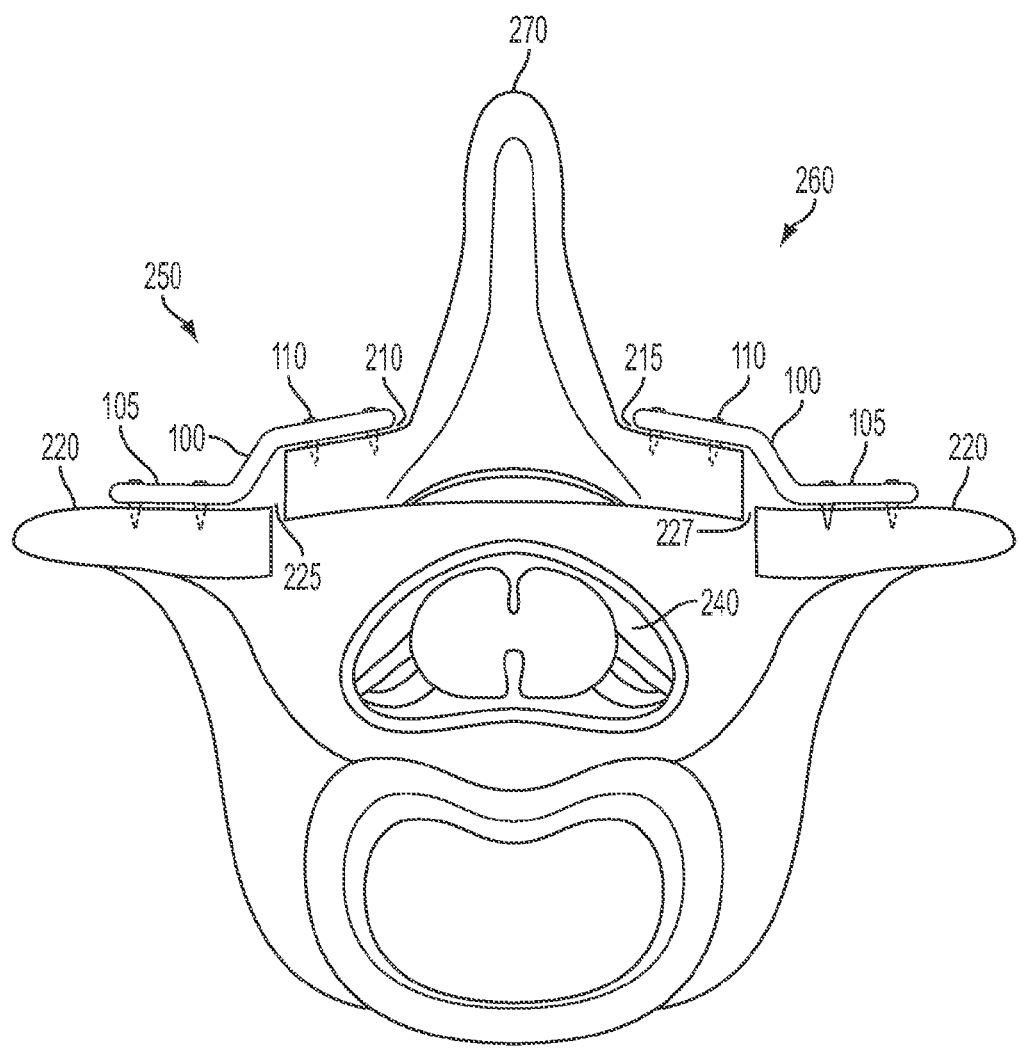
FIG. 3 is a top plan view of the cervical vertebra of FIG. 1, showing the first and second lamina portions in the relief position.
Figure 4:
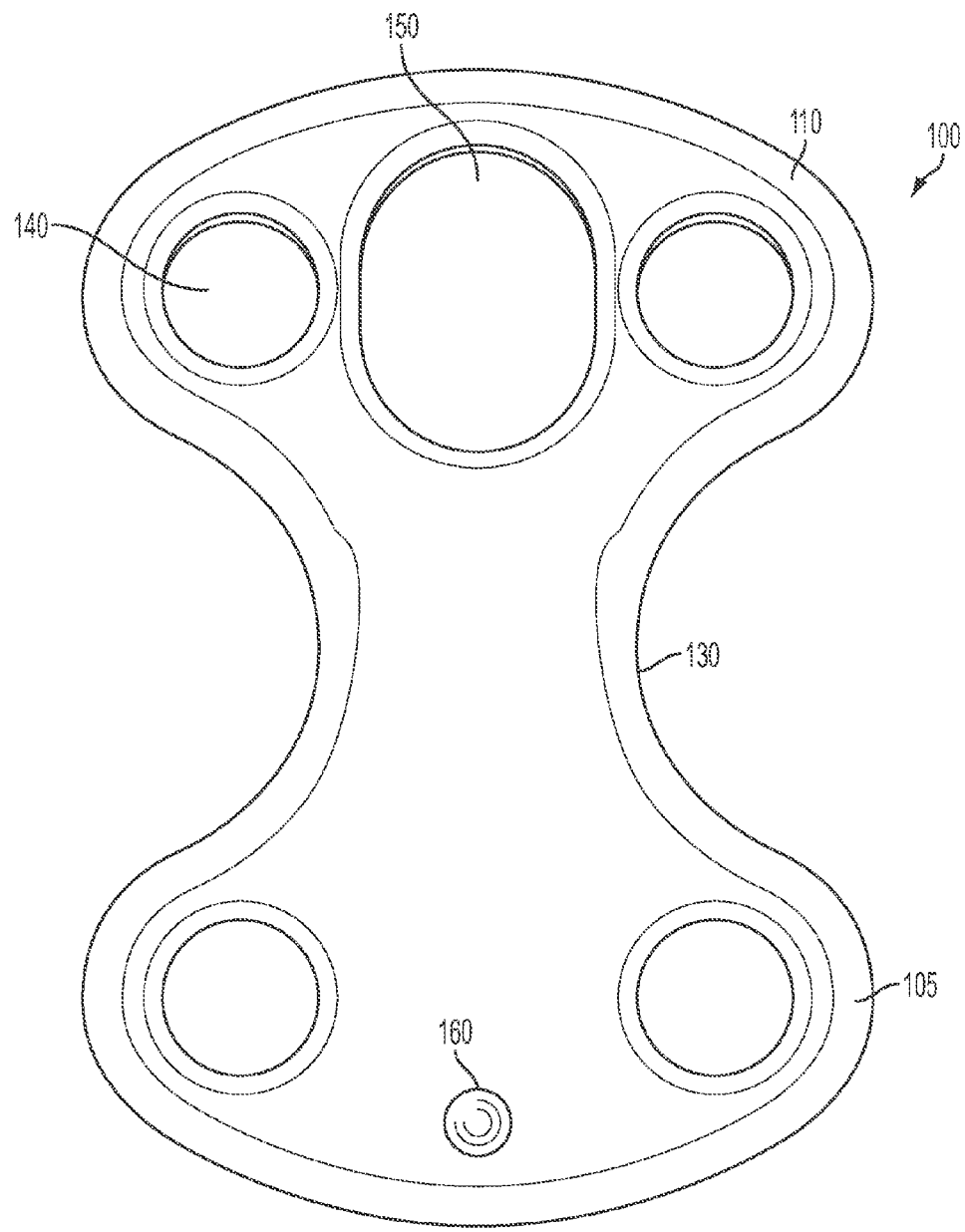
FIG. 4 is a top plan view of an exemplified laminoplasty plate.
Figure 5A:
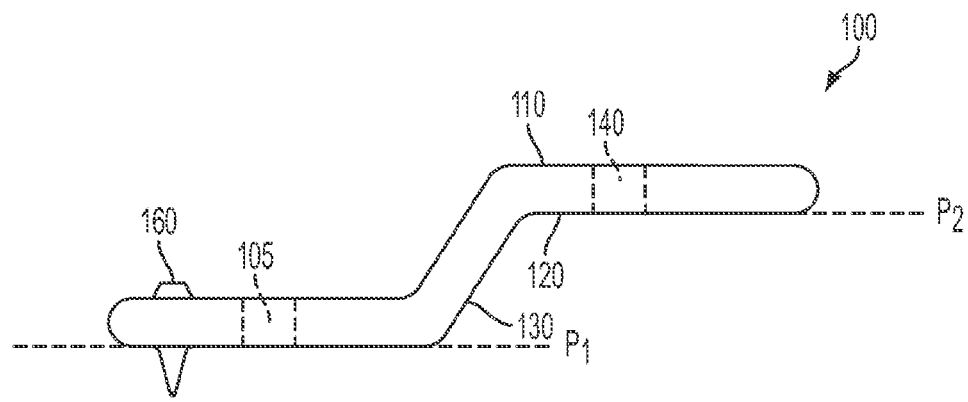
FIG. 5A is a side elevational view of the laminoplasty plate of FIG. 4, showing the first and second planes in parallel.
Figure 5B:
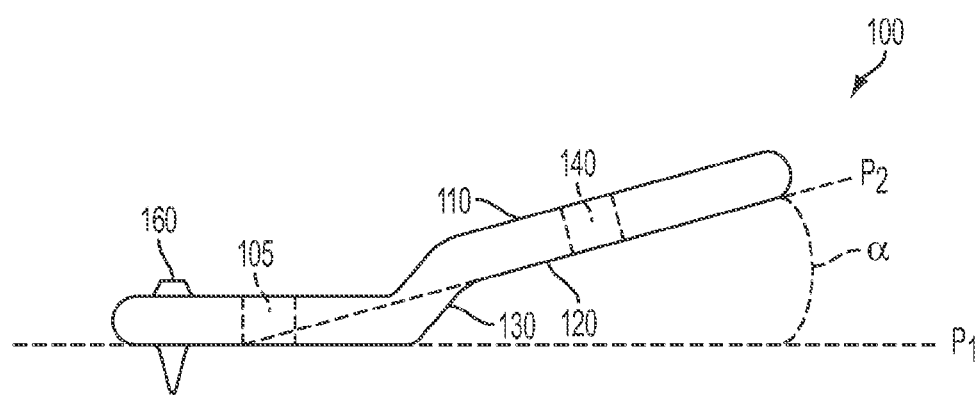
FIG. 5B is a side elevational view of the laminoplasty plate of FIG. 4, showing the first and second planes are at an acute angle relative to one another.
Figure 6:
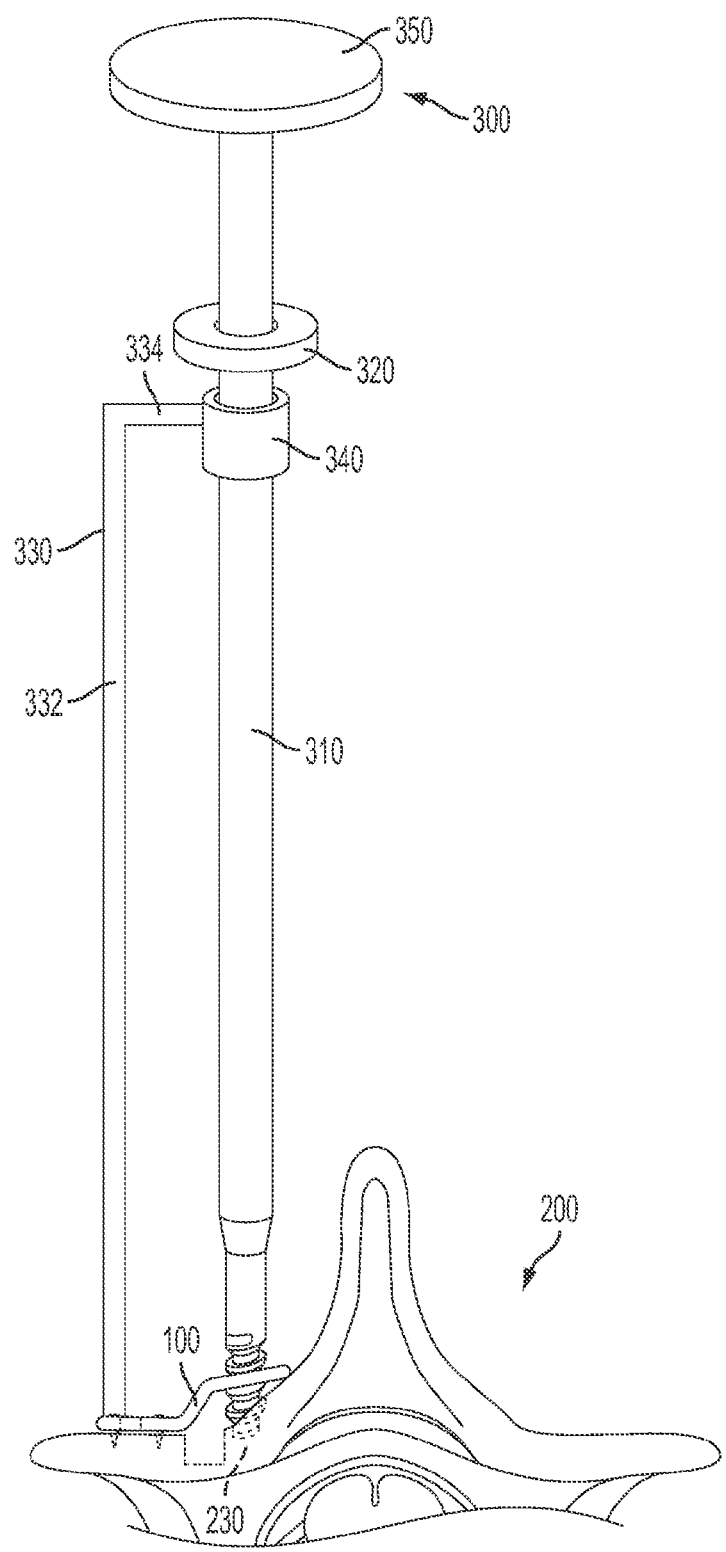
FIG. 6 is a side elevational view of a lamina setting tool.

In one aspect, presented herein is a laminoplasty plate 100 for securing a separated lamina portion 210 of a desired cervical vertebra 200 in a relief position, as shown in FIGS. 2 and 3. In one aspect, the laminoplasty plate 100 comprises a proximal end portion 110 having a bottom surface 120 defined in a first plane $P_1$ and a distal end portion 105 having a bottom surface 120 defined in a second plane $P_2$. In this aspect, the first and second planes are spaced from one another at the medial portion 130 such that the bottom surface of the proximal end portion 110 is spaced from the bottom surface of the distal end portion 105. In one exemplified aspect, the first plane is spaced a predetermined distance of between about 1 mm and about 10 mm. In another example, the first and second planes are spaced between about 3 mm and about 7 mm. In one aspect, the laminoplasty plate can be comprised of biocompatible materials such as, and not meant to be limiting, titanium, titanium alloys, surgical steel, polymeric material, ceramic material, carbon fiber composite, resorbable material, polyglyconate, autograft bone, allograft bone, xenograft bone, and hydroxyapatite.

In one exemplified aspect, the first plane $P_1$ can be substantially parallel to the second plane $P_2$. Alternatively, the first plane can be at an acute angle α relative to the second plane. Preferably, the acute angle is between about 0 degrees and 89 degrees, and more preferably between about 0 degrees and 30 degrees. In another aspect, the laminoplasty plate can comprise a medial portion 130 that is connected to the proximal end portion and the distal end portion. In one exemplified aspect, the medial portion 130 can be arcuate in shape. In another example, the medial portion can have a reduced cross-sectional area relative to the cross-sectional areas of the distal and proximal end portions. As one skilled in the art will appreciate, this reduced cross-sectional area permits the medial portion to be more fully surrounded by bone fusion material. In a further example, the medial portion can be comprised of a substantially rigid material and have an increased cross-sectional area relative to the cross-sectional areas of the distal and proximal end portions. As one skilled in the art will appreciate, this rigidity and increase in cross-sectional area make the laminoplasty plate 100 more resistant to tensile, compressive, or shear loads while allowing the distal and proximal end portions to remain substantially flat.

In one aspect, the laminoplasty plate defines a plurality of bores 140 of pre-determined diameters. In one exemplified aspect, the proximal end portion 110 defines two paired and opposing screw bores 140 that extend substantially transverse therethrough the proximal end portion between the top and bottom surfaces of the proximal end portion and that are configured to operatively receive screws. In another aspect, the proximal end portion also defines a tool screw aperture 150 that extends substantially transverse therethrough the proximal end portion between the top and bottom surfaces of the proximal end portion and is configured to operatively receive a portion of a lamina setting tool 300. In another aspect, the tool screw aperture can be positioned therebetween the pair of screw bores of the proximal end portion. In this aspect, it is contemplated that the tool screw aperture can be positioned adjacent to and equidistant from each screw bore. In a further aspect, the distal end portion defines two paired opposing bores that extend substantially transverse therethrough the distal end portion between the top and bottom surfaces of the distal end portion and is configured to operatively receive screws. It is contemplated that different quantities and positions of the bores of the laminoplasty plate can be used in the present invention.

In one aspect, the distal end portion is comprised of a mountable portion 160 configured for detachably mounting a guide 330. In one exemplified aspect, the mountable portion 160 can be comprised of a raised cone portion to which the guide 330 can be mounted. In another example, the mountable portion can define a cavity to which the guide can be mounted. In another aspect, the mountable portion can define a tool bore 170 for receipt of a portion of the lamina setting tool. In another aspect, the mountable portion can be positioned therebetween the pair of screw bores 140 of the distal end portion 105. In this aspect, it is contemplated that the mountable portion can be positioned adjacent to and equidistant from each screw bore. Further, it is contemplated that different positions and configurations of the mountable portion of the laminoplasty plate 100 can be used in the present invention.

In one aspect, a lamina setting tool 300 is presented for positioning the lamina portion 210 of the desired cervical vertebra 200 in the relief position. In one aspect, the tool comprises a rotatable threaded shaft 310 comprising an adjustable stop 320 and a guide having a body portion 332 and a first support arm 334. In this aspect, the body portion 332 has a fixed length and is spaced therefrom the rotatable threaded shaft. The guide is coupled to the rotatable threaded shaft 310 by the first support arm 334, which is connected to the body portion. At the distal end of the first support arm, the guide is coupled to the rotatable threaded shaft. Further, the body portion of the guide is secured to a stable structure. In one exemplified aspect, the body portion is secured to the desired cervical vertebra substantially on or near the lateral mass 220. In another example, the body portion is secured to a stable structure located within the operating room, such as the operating room table. In another aspect, the rotatable threaded shaft and the body portion of the guide 330 are substantially parallel to one another. In a further aspect, the lamina setting tool can be comprised of biocompatible materials such as, and not meant to be limiting, titanium, titanium alloys, surgical steel, polymeric material, ceramic material, carbon fiber composite, resorbable material, polyglyconate, autograft bone, allograft bone, xenograft bone, and hydroxy-apatite.

In this aspect, the stop 320 is selectively adjustable to correspond to a given limited depth, which will prevent over penetration of the threaded member through the underside of the lamina into the spinal canal 240. In one aspect, the stop is adjustable along the length of the rotatable threaded shaft. In another aspect, the rotatable threaded shaft is attached to the lamina portion at an attachment point 230. In one exemplified aspect, the guide can comprise a second support arm (not shown) that is coupled to the rotatable threaded shaft 310 at a position between the first support arm and the attachment point 230. There may also be a small cylinder 340 connected to the distal end portion of the first support arm. In this aspect, the threaded shaft is configured to fit through and be laterally supported by the small cylinder 340. In another example, the rotatable threaded shaft can comprise a handle portion 350. In this example, the handle portion 350 can be positioned at the top of the rotatable threaded shaft to allow for easy rotation of the rotatable threaded shaft. In a further example, the lamina setting tool comprises a gauge (not shown) calibrated to measure a lift distance. In this example, it is contemplated that the gauge can enable the user of the lamina setting tool to monitor the amount of rotation necessary to achieve a particular lift distance. Specifically, it is contemplated that the gauge can include a means for tracking the number of full rotations of the rotatable threaded shaft, where one full rotation of the rotatable threaded shaft corresponds to a particular lift distance.

Figure 7:
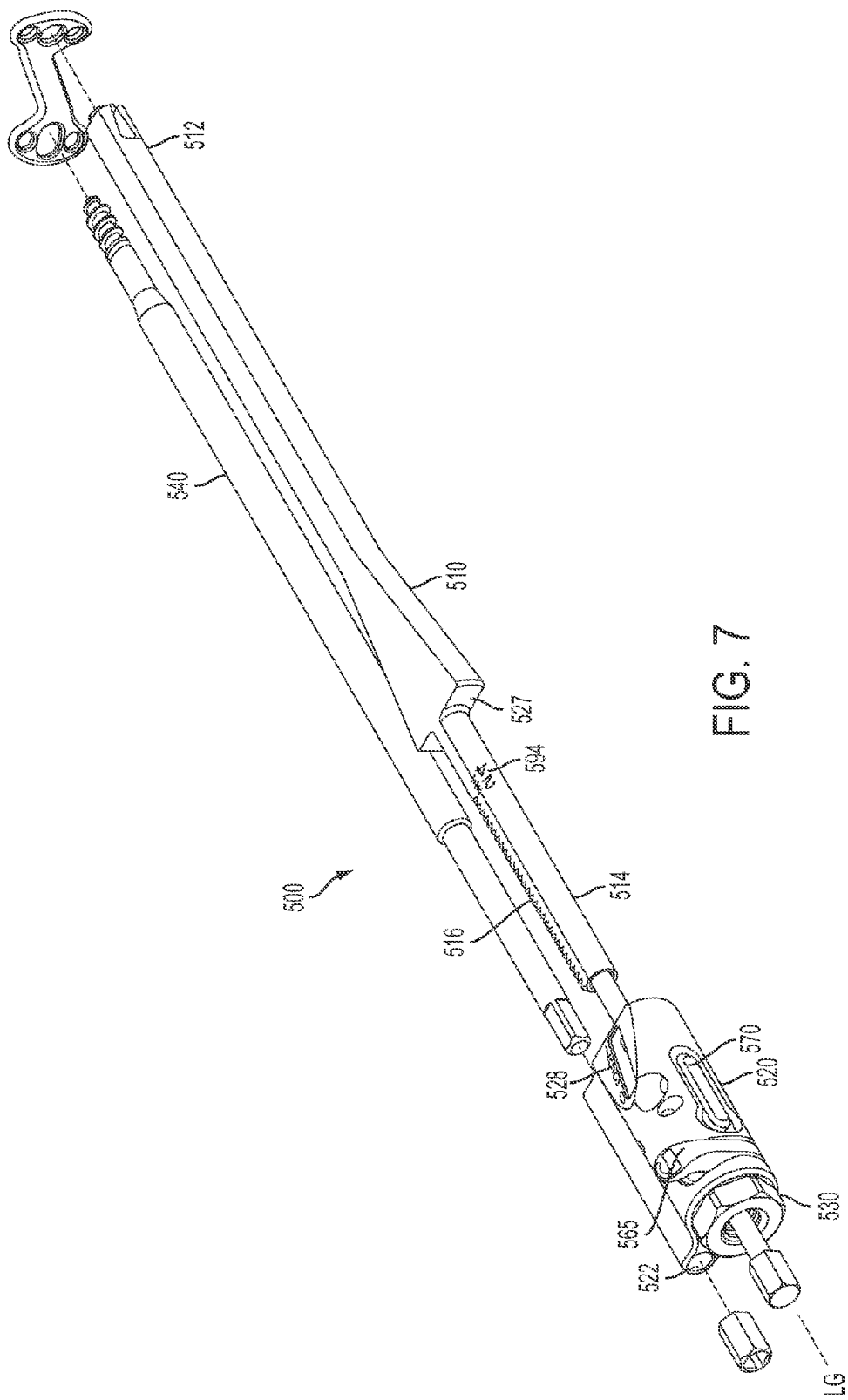
FIG. 7 is a partially exploded perspective view of a lamina setting tool.
Figure 10:
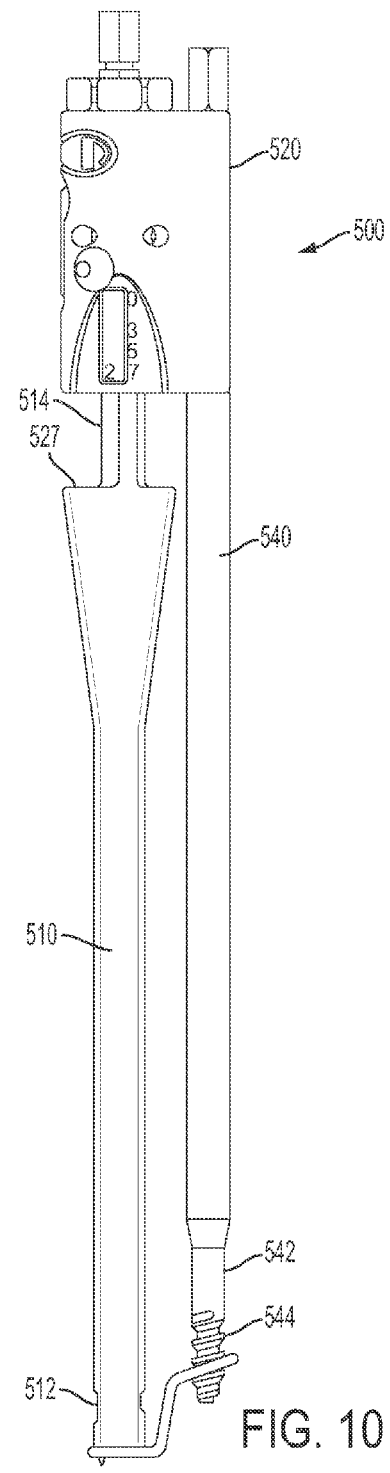
FIG. 10 is a right side elevational view of the lamina setting tool of FIG. 7.
Figure 11:
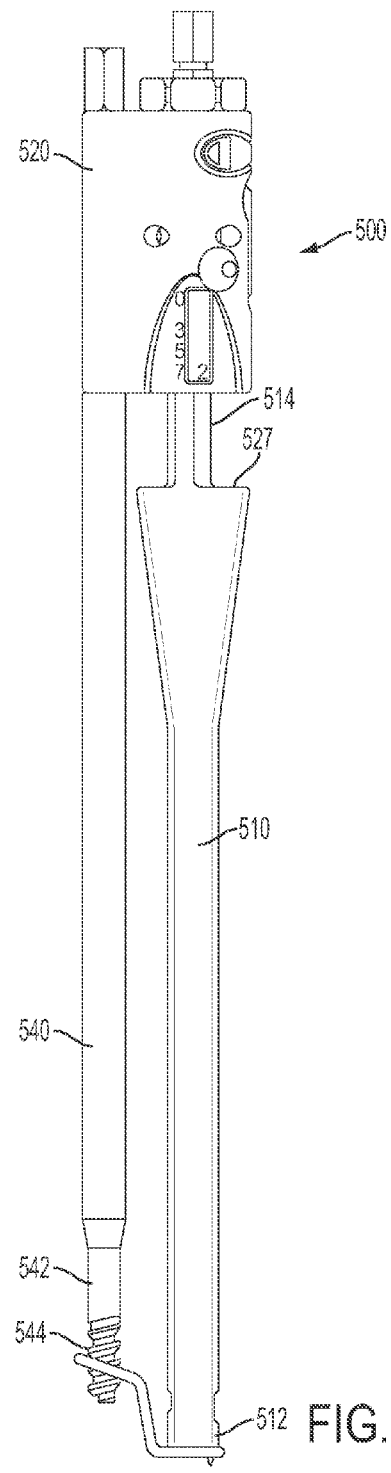
FIG. 11 is a left side elevational view of the lamina setting tool of FIG. 7.

In yet another aspect, the lamina setting tool 500, as shown in FIG. 7, can comprise an elongate guide 510 with a the distal end 512 configured to engage portions of the laminoplasty plate 100 at or near its mountable portion. As illustrated, the lamina setting tool in this aspect comprises a housing 520 that defines a longitudinal channel 522 and an internal chamber 524. The proximal end 514 of the elongate guide is at least partially threaded. A drive nut 530 is disposed in the internal chamber 524 configured for coaxial alignment with the proximal end 514 of the elongate guide 510. The drive nut 530 has internal threads 532 to selectively engage at least a portion of the threads disposed thereon the proximal end 514 of the elongate guide. The bore 534 of the drive nut 530 is sized such that it can be moved laterally into and out of engagement with the threads disposed thereon the proximal end of the elongate guide 510. It is configured to move from a first non-engaged position, where the housing can freely move along the longitudinal axis $L_G$ of the elongate guide and, to a second engaged position, where the housing can move in a controlled manner along the longitudinal axis of the elongate guide by rotating the drive nut in either a clockwise or counterclockwise manner.

In one aspect, the lamina setting tool 500 comprises an elongate bone screw shaft 540 partially retained within the longitudinal channel 522 of the housing. The bone screw shaft 540 is configured for rotation within the longitudinal channel. As can be seen in FIG. 8, the distal end 542 of the bone screw shaft 540 comprises threads 544 for boring into a portion of a lamina of the desired cervical vertebra. In another aspect, the elongate guide 510 and the elongate bone screw shaft 540 are substantially parallel.

As mentioned, in one aspect, in the non-engaged position, the housing can freely move along the longitudinal axis of the elongate guide 510. As such, in one aspect, there is a stop mechanism 527 positioned thereon the elongate guide 510 substantially adjacent the proximal end 514 of the elongate guide to limit longitudinal movement of the housing toward the distal end 512 of the elongate guide.

In still another aspect, the lamina setting tool can also have at least one bias element 550 positioned therein the internal chamber 524 of the housing substantially transverse to and external of the exterior portion 536 of the drive nut 530. The bias element can be, for example and not meant to be limiting, a spring. The bias element is designed, in this aspect, to bias the drive nut into engagement with at least a portion of the threads disposed thereon the proximal end of the elongate guide 510. Therefore, in the normal position, the drive nut would be in the engaged position.

To work with the bias element 550, in one aspect, the housing can define a lockslide recess 560 positioned substantially tangential to the exterior portion of the drive nut. Disposed therein the lockslide recess 560 is a lockslide 565 that has a ramped surface 567 configured to wedge against the exterior portion 536 of the drive nut and move it from the first non-engaged position to the second engaged position. The ramped surface can, for example, have a plurality of curved ramped surfaces to conform to a portion of the exterior portion of the drive nut.

In one exemplified aspect, the elongate bone screw shaft 540 is substantially restricted from longitudinal movement with respect to the channel. Thus, it moves longitudinally with the housing with respect to the elongate guide 510.

In another example, the drive nut can define a recess 538 in its exterior surface 536. The housing, in this aspect, can have a rocker arm aperture 526 defined therein that is longitudinally aligned with the recess 538 of the drive nut. As such, there can be a rocker arm 570 having a proximal end 572 hingedly affixed to an external portion 529 of the housing 520 and a distal end 574 positioned therethrough the rocker arm aperture 526. The distal end of the rocker arm can move into and out of engagement with the recess, as the recess rotates with the drive nut. In this manner, at least one time per revolution of the drive nut, the distal end of the rocker arm is disposed within the recess. This configuration gives the user a tactile sense of the relative movement of the housing, and thus the elongate bone screw shaft, to the elongate guide, as each rotation of the lock nut represents differential movement of the housing with respect to the elongate guide, depending upon the thread pitch of the threads on the proximal end of the elongate guide and the internal threads of the drive nut.

Figure 12:
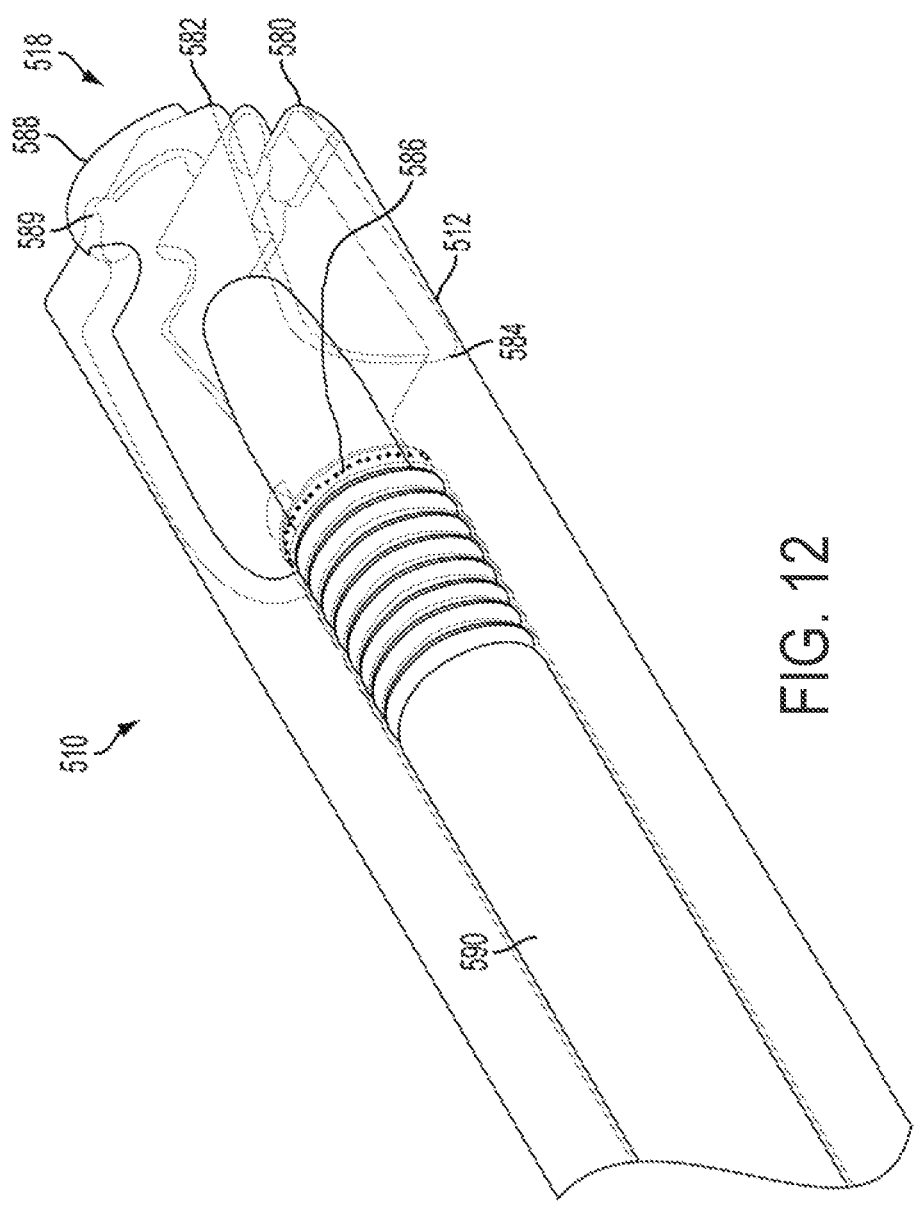
FIG. 12 is a partially transparent perspective view of the distal end of the elongated guide of the lamina setting tool of FIG. 7.
Figure 13:
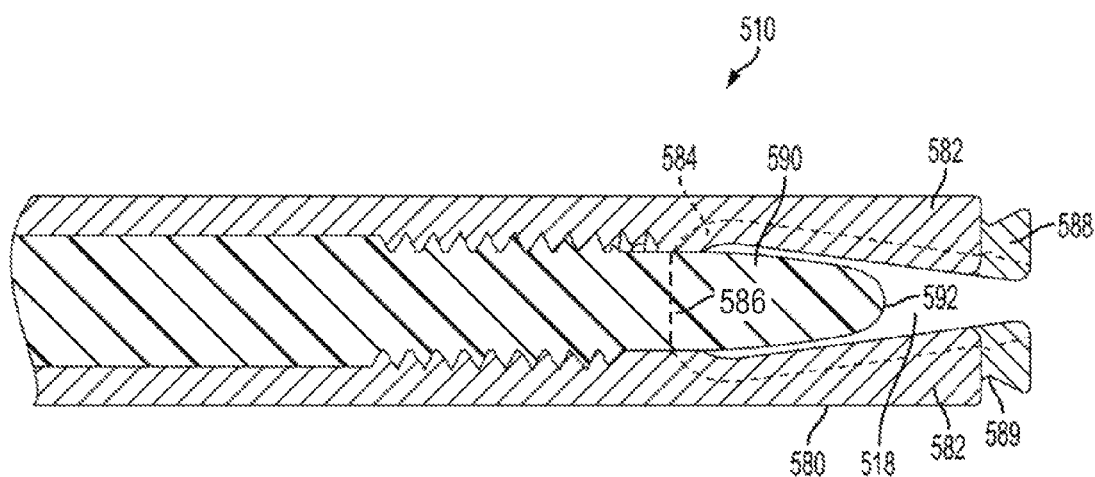
FIG. 13 is a cut away side elevational view of the distal end of the elongated guide of the lamina setting tool of FIG. 7.
Figure 14:
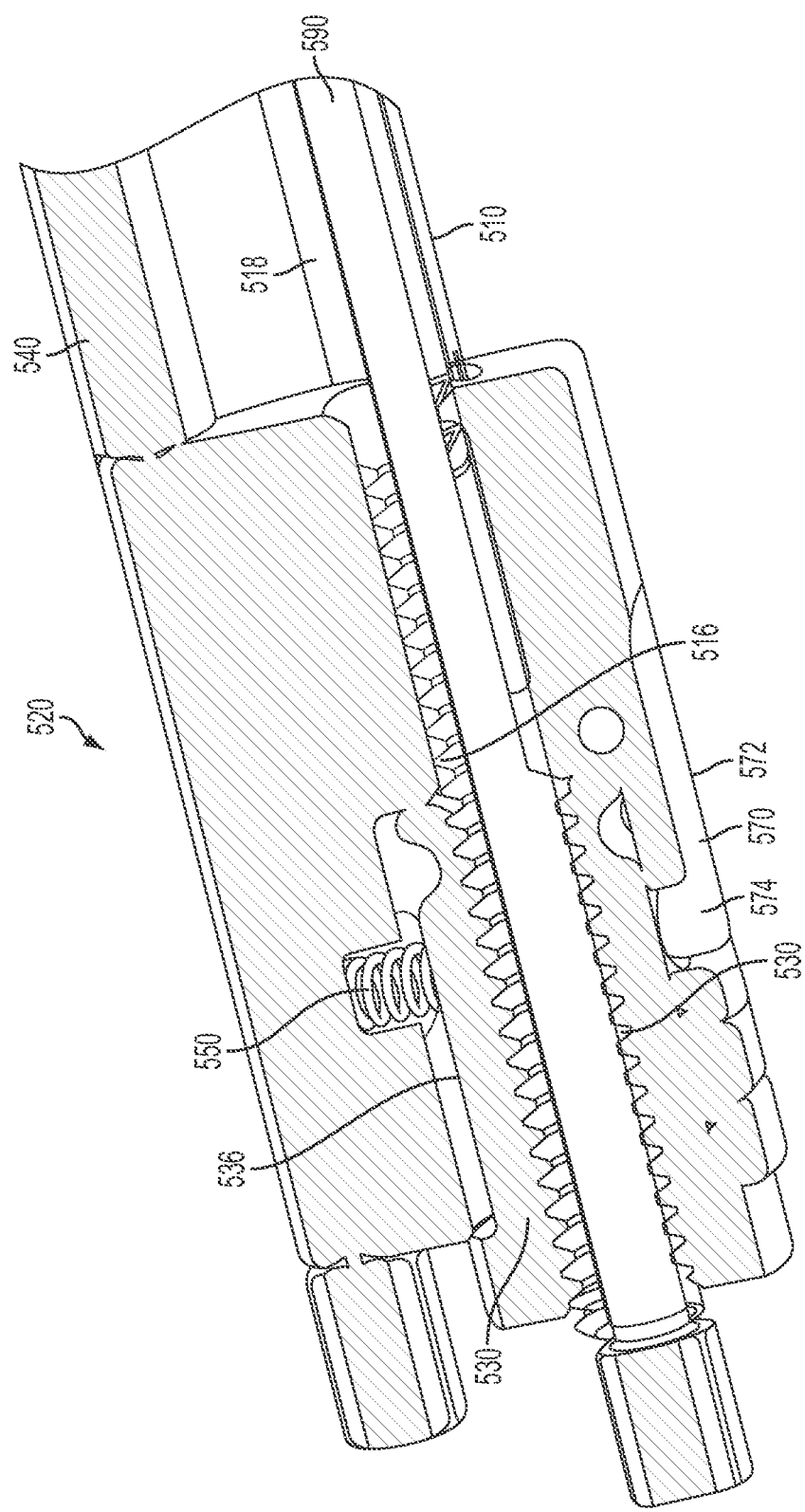
FIG. 14 is a cut away perspective view the housing of the lamina setting tool of FIG. 7.
Figure 15:
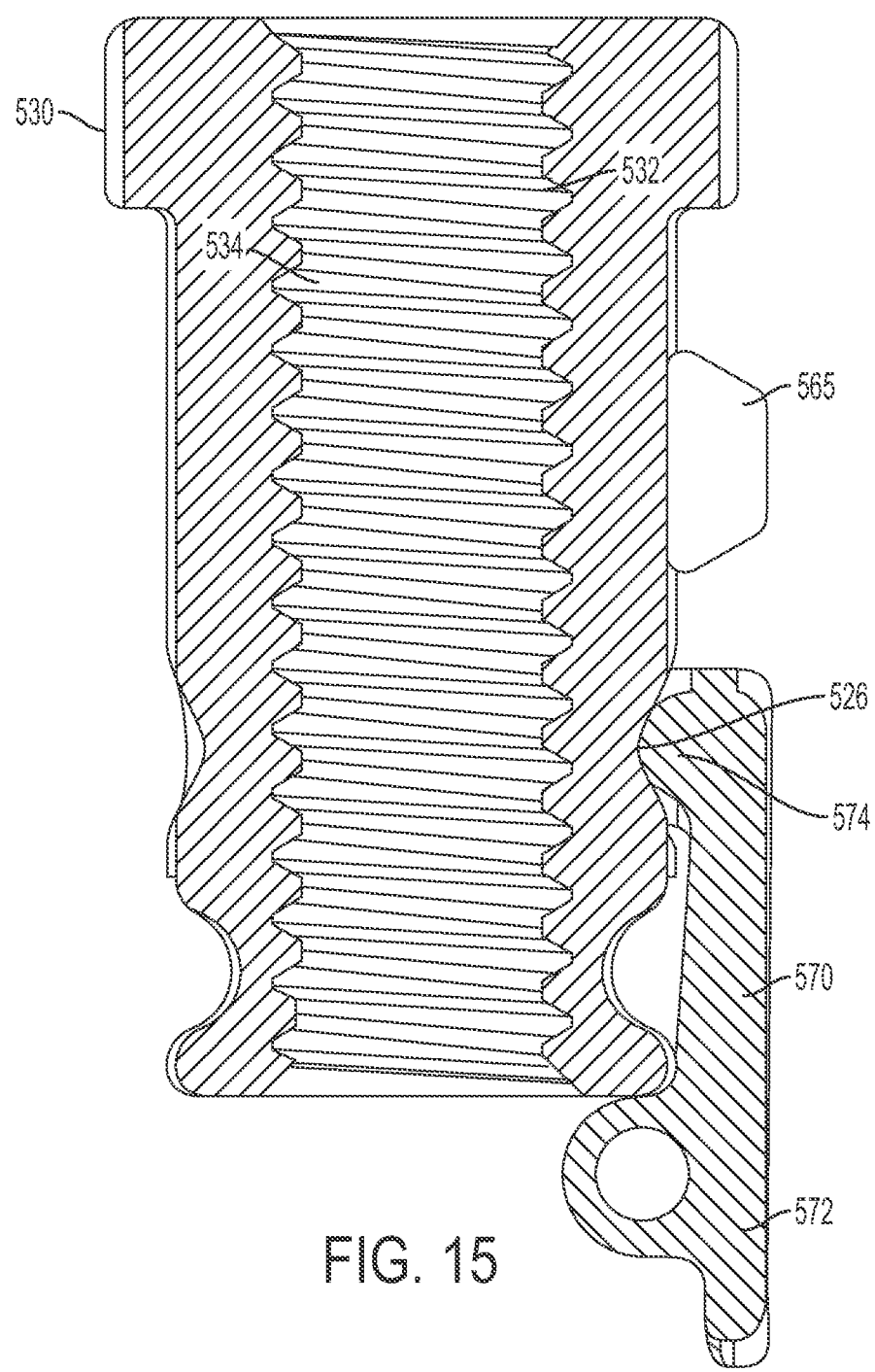
FIG. 15 is a cut away side elevational view of the drive nut of the lamina setting tool of FIG. 7.
Figure 16:
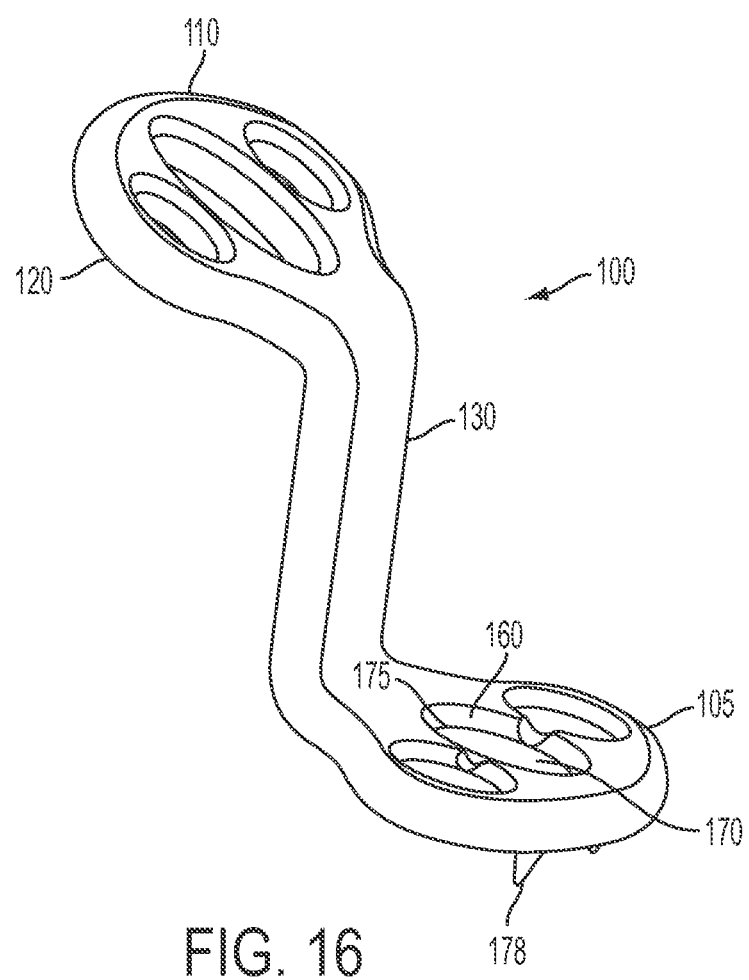
FIG. 16 is a perspective view of one aspect of a laminoplasty plate.
Figure 17:
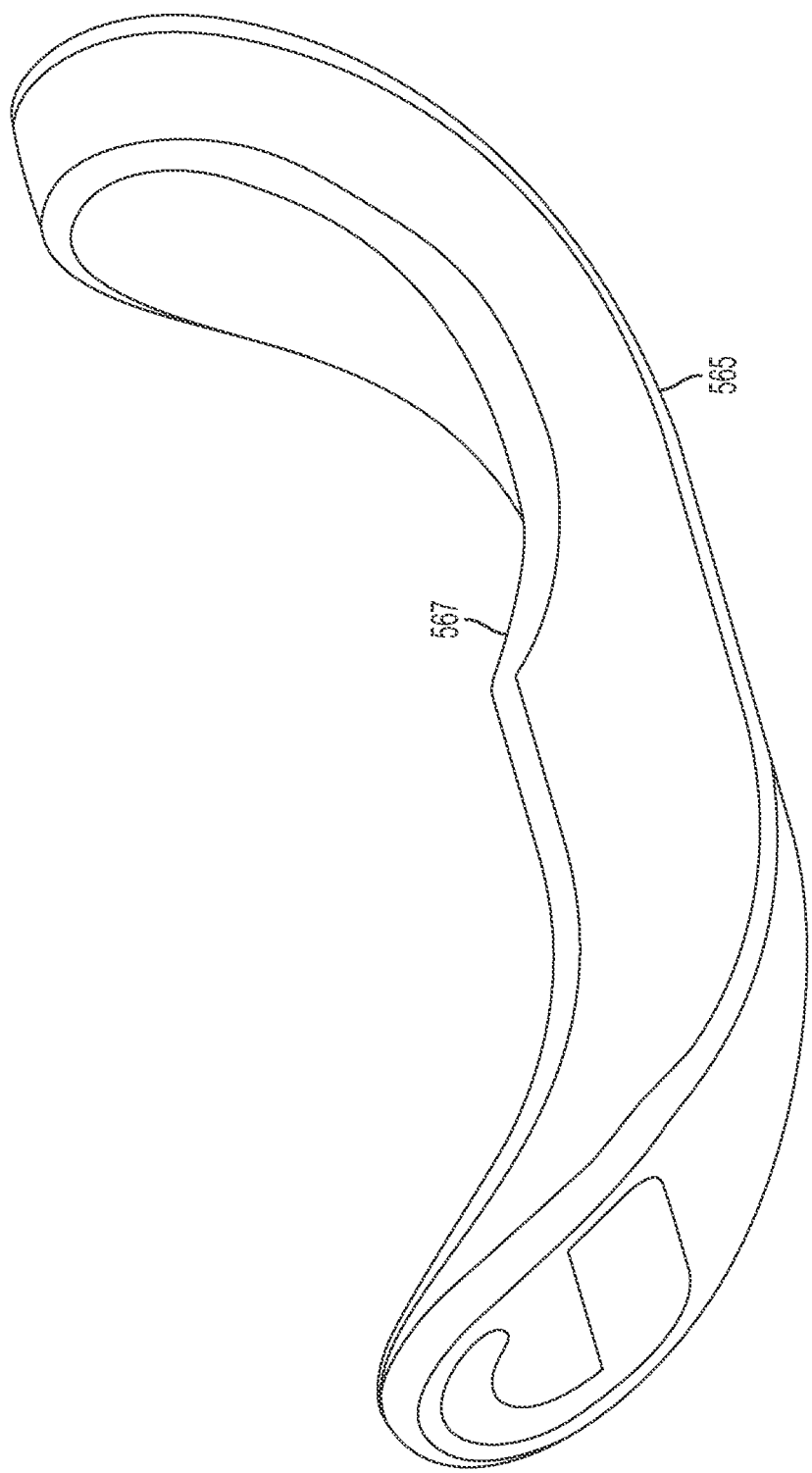
FIG. 17 is a perspective view of one aspect of a lockslide for a lamina setting tool.
Figure 18:
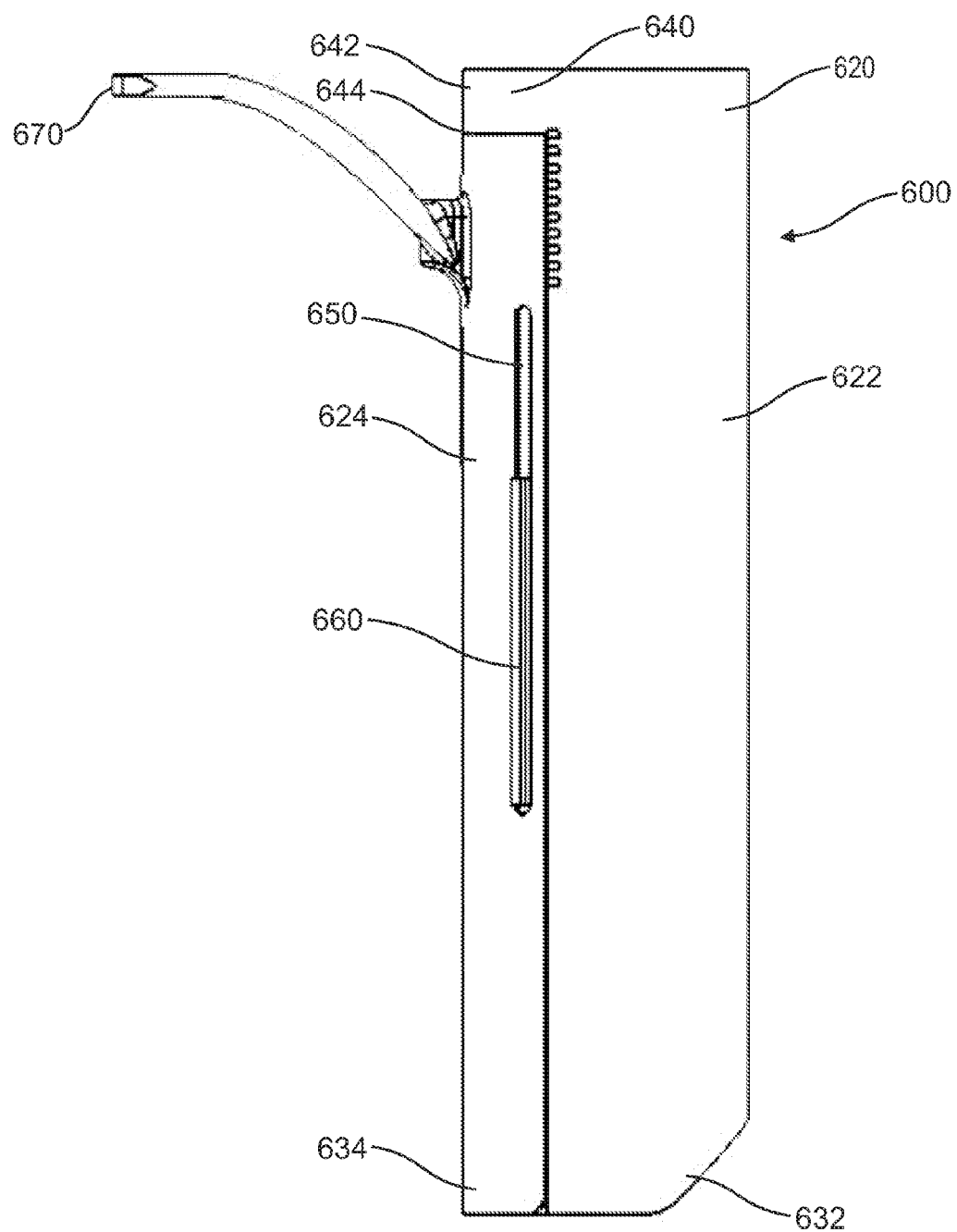
FIG. 18 is a side elevational view of one aspect of a laminoplasty portal in a first position.
Figure 19:
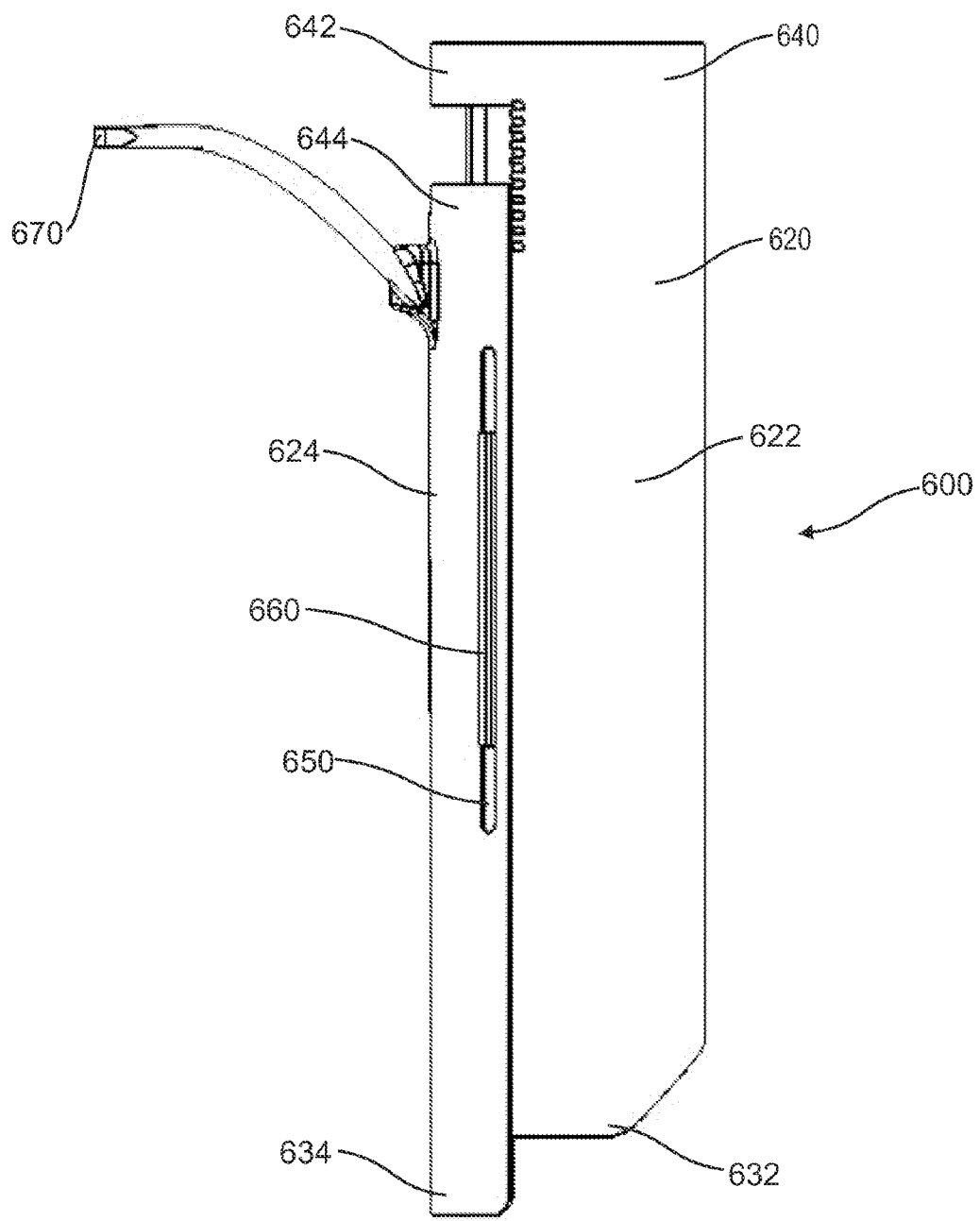
FIG. 19 is side elevational view of one aspect of the laminoplasty portal of FIG. 18, in a second, elevated, position.
Figure 20:
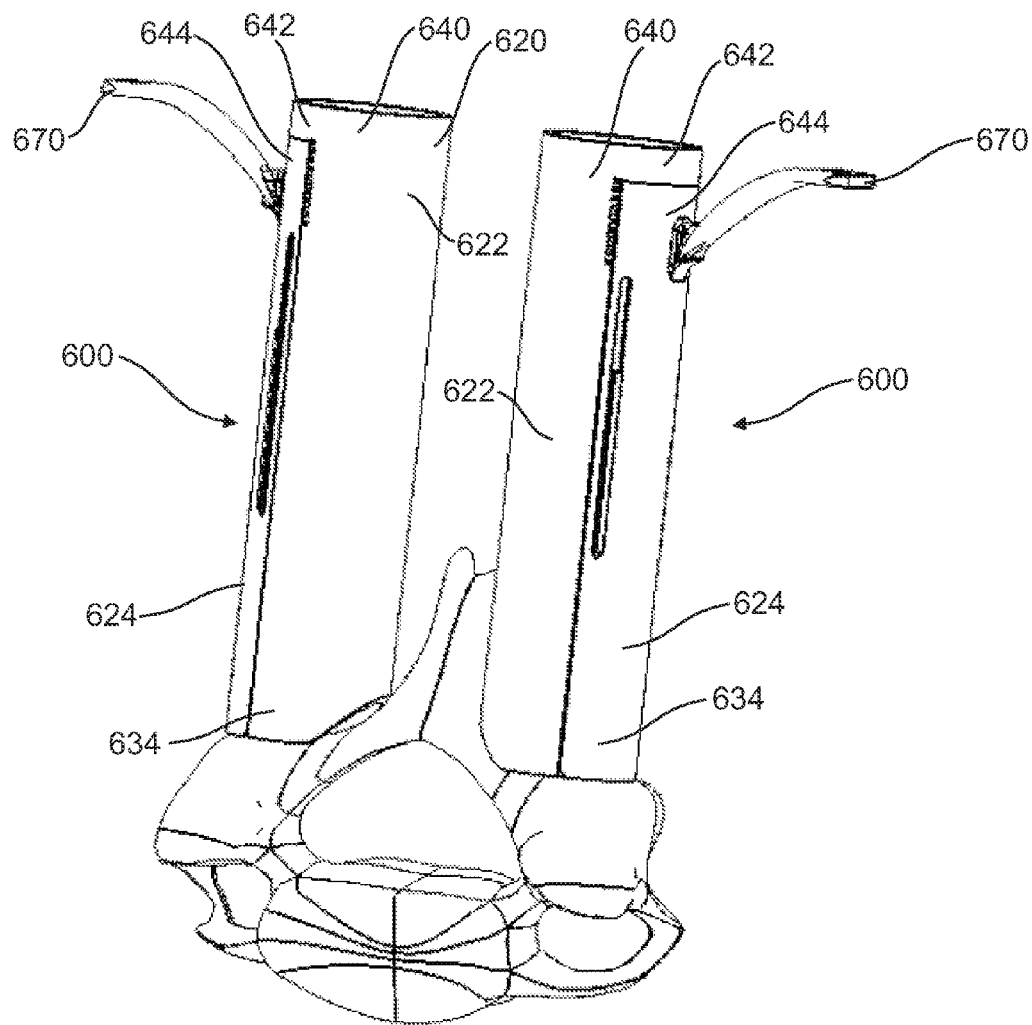
FIG. 20 is a perspective view of one aspect of two laminoplasty portals shown in-situ in the first position.
Figure 21:
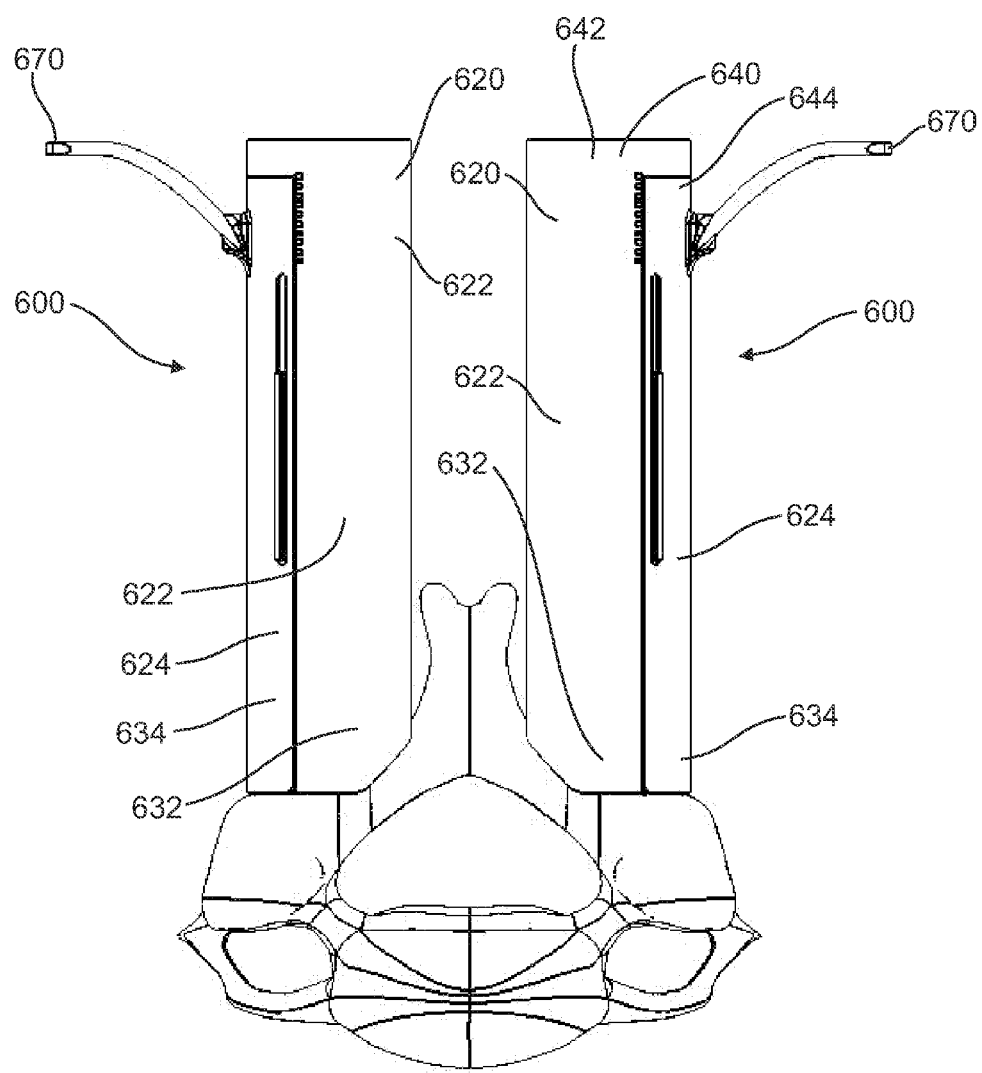
FIG. 21 is a side elevational view of one aspect of two laminoplasty portals shown in-situ in the first position.
Figure 22:
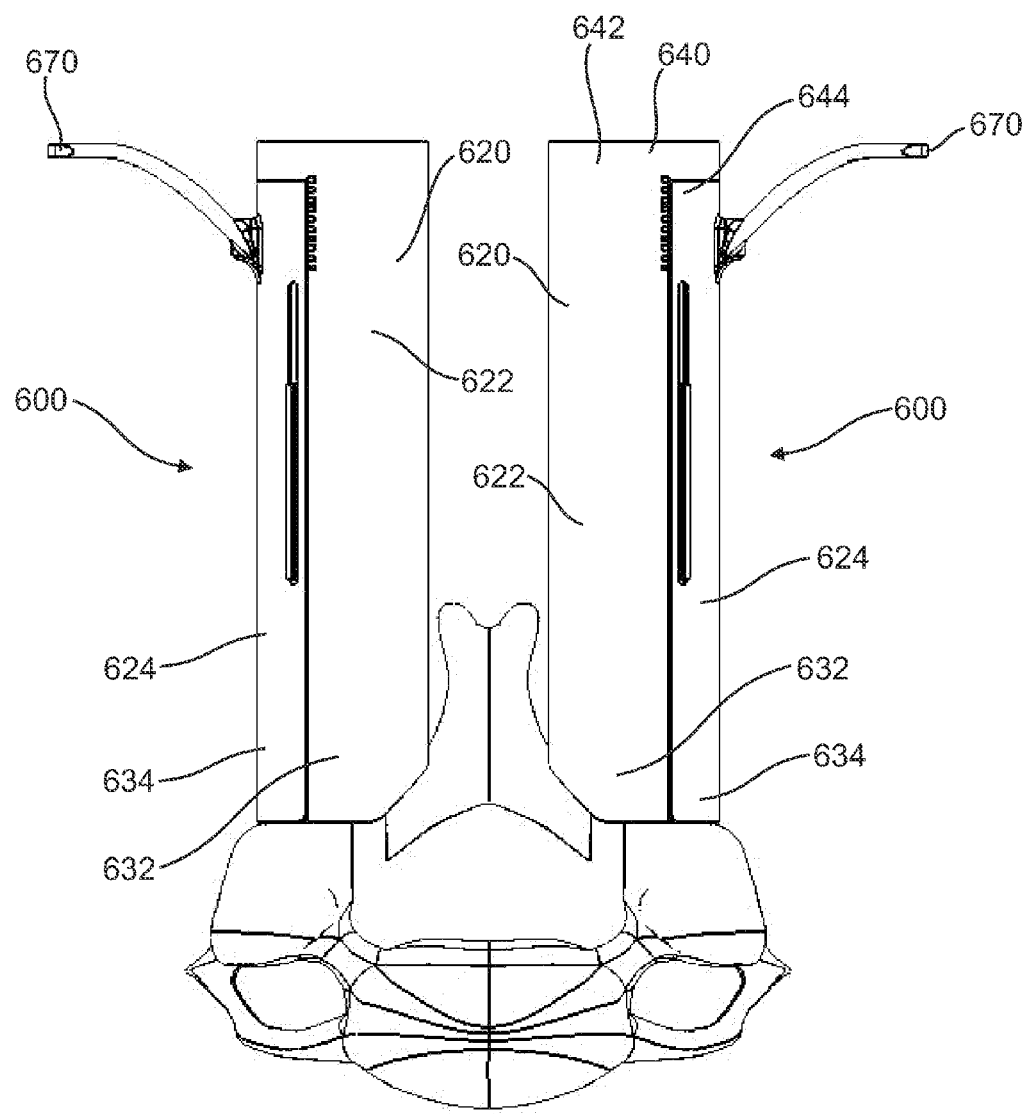
FIG. 22 is a side elevational view of one aspect of two laminoplasty portals shown in FIG. 21 in the first position, showing portions of the lamina removed.
Figure 23:
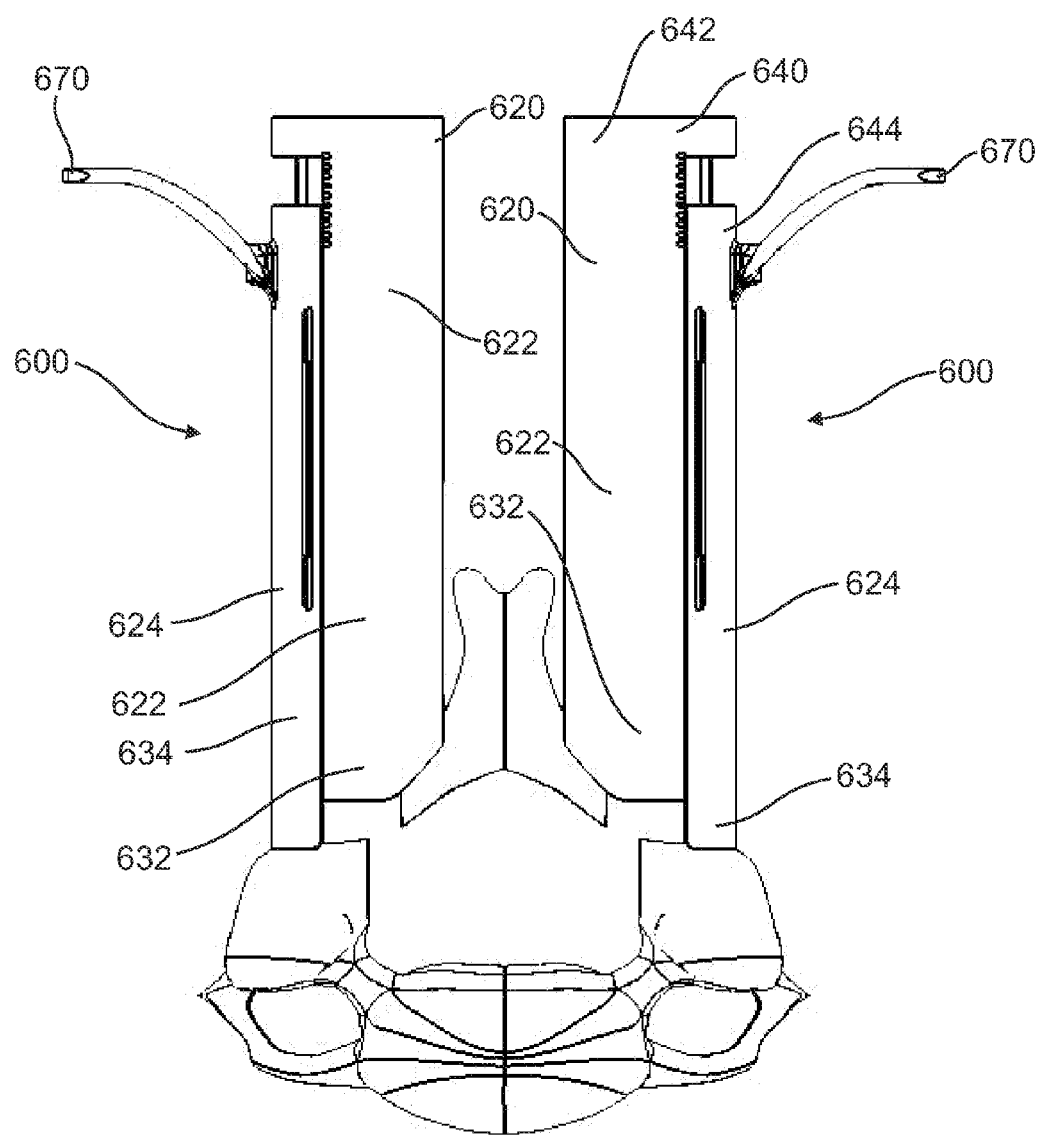
FIG. 23 is a side elevational view of one aspect of two laminoplasty portals shown in FIG. 21 in the second, elevated position.
Figure 24:
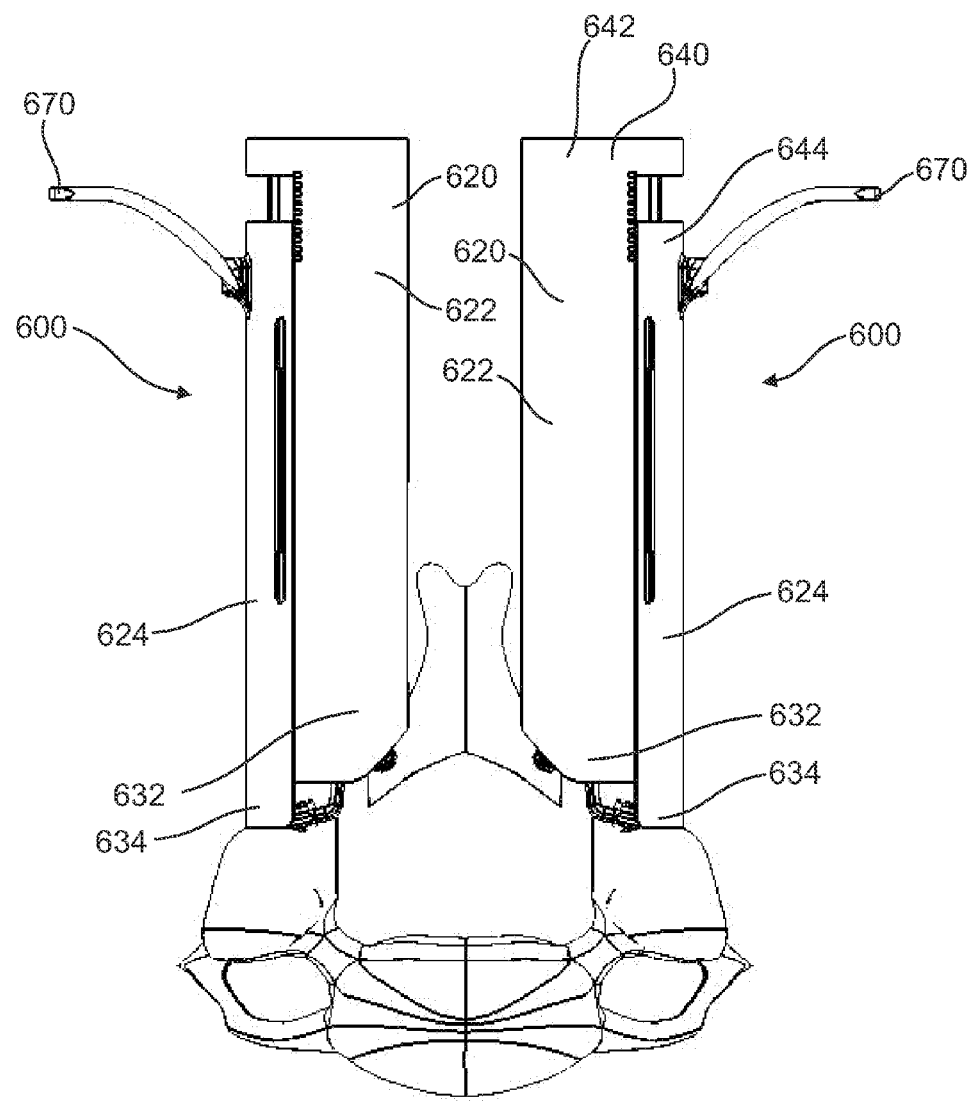
FIG. 24 is a side elevational view of one aspect of two laminoplasty portals shown in FIG. 21 in the second, elevated position, showing a pair of laminoplasty plates positioned adjacent first and second sagittal divisions.

In one aspect, the elongate guide 510 can be substantially tubular, defining an internal longitudinal shaft cavity 518. In this aspect, the distal end of the elongate guide 512 comprises a tip 580 with an inwardly tapered horseshoe cross-sectional shape with two leg portions 582 and a seat portion 584 that defines a seat aperture 586, as illustrated in FIG. 12. The external portion of the tip 588 is configured to mate with an interior portion 175 of the tool bore 170 of the laminoplasty plate. In this aspect, an elongate rod 590 is disposed within the shaft cavity 518. The elongate rod has a distal end portion 592 that is configured to move longitudinally therethrough the seat aperture 586 to selectively splay the two leg portions 582 away from each other. As the outer diameter of the tip of the guide is increased, it causes the external portion 588 of the tip to frictionally engage the tool bore 170. In one aspect, the external portion of the tip also has a circumferential ridge 589 within which the interior portion of the tool bore can mate. As illustrated, in one aspect, the distal end portion 592 of the elongate rod is threaded and configured to engage the seat aperture such that rotation of the elongate rod 590 causes the distal end portion of the elongate rod to protrude into and retract from engagement with the two leg portions, spaying the leg portions in one direction and allowing them to retract to the normal position in the other direction.

As can be seen in FIG. 8, the lamina setting tool 500 in this aspect can comprise graduated markings 594 on the external portion of the elongate guide 510, as well as on the housing to display visually the boring depth of the distal end 542 of the elongate bone screw shaft 540 into the portion of a lamina of a cervical vertebra, and to assist in determining the relative longitudinal location of the elongate bone screw shaft with respect to the elongate guide 510.

Also presented herein are methods of treating cervical stenosis in a patient by relieving spinal cord compression. In one aspect, at least a portion of the desired cervical vertebra, which defines a spinal canal 240 having a pre-operative cross-sectional area, is exposed. To do so, in one aspect, a posterior incision in the patient over an area of cervical stenosis of the patient is made to expose the posterior side of the desired cervical vertebra. In this aspect, a small pathway, ranging from about 14 to 18 mm, can be dilated through the soft tissue to reach the desired cervical vertebra 200 so that muscle and tissue damage is kept to a minimum. In another aspect, the spine may be exposed more extensively in the traditional open approach.

In another aspect, the first lamina portion of the desired cervical vertebra is separated. In one exemplified aspect, the step of separating the first lamina portion 210 of the desired cervical vertebra comprises making a first sagittal division 225 from the exterior of the desired cervical vertebra to the spinal canal on a first side of the midline of the vertebra and making a second sagittal division 227 from the exterior of the desired cervical vertebra to the spinal canal on a second side of midline 260. Thus, the lamina portion 210 of the desired cervical vertebra 200 and the spinous process 270 will no longer be attached at any point to the remainder of the desired cervical vertebra. In one aspect, the first and second sagittal divisions are made at the junction between the lamina portion and the lateral mass portion.

In another aspect, the first lamina portion is controllably elevated to a relief position in which the spinal canal of the desired cervical vertebra has a relief cross-sectional area that is greater than the pre-operative cross-sectional area, wherein the first lamina portion is subsequently secured in an elevated position. In this aspect, after providing at least one laminoplasty plate, the step of controllably raising the first lamina portion 210 to a relief position can first comprise attaching at least a portion of the distal end portion of a first laminoplasty plate to a portion of the first lateral mass portion of the desired cervical vertebra adjacent the first sagittal division 225 and attaching at least a portion of the proximal end portion of the first laminoplasty plate to a first lamina portion adjacent the first sagittal division. In this aspect, a pre-determined length of the medial portion 130 of the laminoplasty plate 100 can correspond to the amount of separation needed between lamina portion and the desired cervical vertebra. The step of controllably raising the second lamina portion 215 to the relief position can then comprise attaching at least a portion of the distal end portion of a second laminoplasty plate to a second lateral mass portion of the desired cervical vertebra adjacent the second sagittal division 227 and attaching at least a portion of the proximal end portion 110 of the second laminoplasty plate to a second lamina portion adjacent the second sagittal division. In one exemplified aspect, the laminoplasty plates can be attached to the desired lateral mass portion and lamina portion with screws. In this example, the screws can be conventional self-tapping bone screws. It is also contemplated that conventional non-self-tapping bone screws can be used in the method of the present invention. In one aspect, the step of attaching the distal end portion 105 of the laminoplasty plates to the desired cervical vertebra comprises attaching the distal end portion of the laminoplasty plates to the respective lateral mass of the cervical vertebra. It is also contemplated that the steps of the method described herein can be completed on the first side of the midline and the second side of the midline simultaneously, sequentially, or in an alternating fashion.

In a further aspect, the lamina setting tool 300 can be provided to assist with the step of controllably raising and securing the lamina portion in the relief position. In this aspect, the guide is configured to detachably mount the mountable portion 160 of the laminoplasty plate 100. In one exemplified aspect, the guide can comprise a hollow shank portion configured to interlock with the raised cone portion of the distal end portion of the laminoplasty plate. In another example, the guide can comprise a mounting edge adapted to be secured within the cavity of the distal end portion. It is contemplated that the present invention can encompass alternative means for mounting the guide to the mountable portion of the laminoplasty plate.

As noted above, the laminoplasty plate comprises a proximal end portion that can define a tool screw aperture 150 configured for operative receipt of the lamina setting tool. In one aspect, the rotatable threaded shaft 310 of the lamina setting tool is configured for insertion into the tool screw aperture. In this aspect, the distance between the rotatable threaded shaft and the body portion 332 of the guide 330 can be equal to the distance between the tool screw aperture and the mountable portion of the distal end portion.

In one exemplified aspect, the lamina portion 210 of the desired cervical vertebra is separated by making a first sagittal division from the exterior of the desired cervical vertebra 200 to the spinal canal on a first side of the midline of the spinous process 270 and making a second sagittal division from the exterior of the desired cervical vertebra to the spinal canal on a second side of midline. In one aspect, the second sagittal division may be a partial thickness division, leaving a portion of the second portion of the lamina partially intact. In this aspect, only the first laminoplasty plate would be used and the second sagittal division 227 would substantially hinge, permitting movement of the first lamina portion 210.

Following the complete or partial separation of the lamina portion, the distal end portion of a first laminoplasty plate is secured to the portion of the desired cervical vertebra adjacent the first sagittal division. If the initial separation of the lamina portion is partial, it is completed after having secured the threaded shaft to the lamina in the following steps. In this manner, the lamina remains stable to the vertebra during the process of mechanically securing it with the threaded shaft. The guide detachably mounts the mountable portion 160 of the first laminoplasty plate. In this aspect, the surgeon can line up the rotatable threaded shaft with the tool screw aperture on the proximal end portion of the first laminoplasty plate. The surgeon rotates the rotatable threaded shaft through the tool screw aperture and through the lamina portion until the stop contacts the first support arm of the guide at an interference point. At this point, further rotation of the rotatable threaded shaft controls the elevation of the first lamina portion, although it is contemplated that the lamina portion can be elevated in other manners. Accordingly, during this process, the stop must be securely attached to the rotatable threaded shaft such that further insertion of the rotatable threaded shaft into the lamina portion is prevented. In this aspect, the surgeon rotates the rotatable threaded shaft until the top surface of the lamina portion is substantially flush with the bottom surface 120 of the proximal end portion of the first laminoplasty plate. The proximal end portion of the first laminoplasty plate is then secured to the lamina portion, wherein the lamina portion is fixed in the relief position. It is contemplated that this procedure can then be completed on the second side of midline 260 about the second sagittal division through the use of a second laminoplasty plate, if a complete division of the lamina is performed bilaterally. In this case, the procedure may be performed one after the other, simultaneously or in a step-wise manner on both sides.

In another aspect, the rotatable threaded shaft has an outer diameter and an inner diameter, with the outer diameter being smaller than the pre-determined diameter of the bore configured for operative receipt of the lamina setting tool. In this aspect, the rotatable threaded shaft has a thread-pitch equal to the distance between the threads along the shaft. The thread pitch can be determined once the outer and inner diameters of the rotatable threaded shaft are known, with the range of outer diameters preferably falling between 0 and 16 mm, more preferably between 1 and 4 mm, and with the range of inner diameters preferably falling between 0 and 14 mm, more preferably between 0.5 and 3.5 mm. Under these constraints, the thread pitch will preferably fall between 0 and 4 mm, more preferably between 0.25 and 2 mm. As one will appreciate, the thread-pitch can be used to determine the amount of rotation of the rotatable threaded shaft 310 required to accomplish a given lift distance. Accordingly, the gauge of the lamina setting tool 300 can be calibrated based on the thread-pitch of the rotatable threaded shaft.

In another aspect, the step of attaching the rotatable threaded shaft to the lamina portion comprises drilling a hole in the first and second sides of midline adjacent the first and second sagittal divisions and screwing the rotatable threaded shaft into the holes defined by the first and second sides of midline. As one skilled in the art will appreciate, the diameter of the drilled holes must be large enough to allow for the insertion of the rotatable threaded shaft and small enough to allow the threads to engage the lamina.

In a further aspect, the lamina setting tool 500 can be provided to assist with the step of controllably raising and securing the lamina portion in the relief position. In this aspect, the laminoplasty plate can be secured to the tip of the elongate guide 510 by placing the tip into the tool bore 170 of the laminoplasty plate and splaying the legs of the tip into frictional engagement with the interior portion 175 of the tool bore 170. Using the guide, the laminoplasty plate can be positioned onto a lateral mass portion of the desired cervical vertebra, adjacent a partial sagittal division which has already been performed substantially at the junction between the lateral mass and the lamina. To assist in holding the laminoplasty plate in position, the laminoplasty plate can comprise one or more spikes 178 protruding from the bottom surface of the distal end portion of the plate. The laminoplasty plate can then be secured to the lateral mass using screws.

In an exemplified aspect, the housing can be placed onto the elongate guide by placing the lock nut in the non-engaged position and sliding over the proximal end of the elongate guide, ensuring that the elongate bone screw shaft is coaxial with the tool screw aperture 150. Keeping the lock nut in the non-engaged position, the elongate bone screw shaft can then be driven into the lamina to the desired depth. By knowing the distance between the first and second planes of the laminoplasty plate, the markings on the housing and the external portion of the elongate guide 510, the surgeon can determine the depth of the distal end of the elongate bone screw shaft.

In this aspect, the lamina can be completely separated at the sagittal division from the lateral mass. At this point, the drive nut can be placed in the engaged position. In one aspect, this can be completed by repositioning the lockslide to overcome the force of the bias element. The lamina can now be controllably raised by rotating the drive nut and raising the elongate bone screw shaft with respect to the elongate guide.

Once the lamina is raised to the relief position, as indicated by the markings 528 on the housing and markings 594 on the external portion of the elongate guide, it can be secured into position by placing screws into the screw bores on the proximal end portion of the laminoplasty plate. Once secured, the elongate bone screw shaft can be removed, as well as the elongate guide. As one skilled in the art can appreciate, these steps can be varied with respect to sequence by the surgeon, as needed. The method can also be performed bilaterally or using the aforementioned open door procedure.

In one exemplified aspect, a graft (not shown) is placed proximate at least a portion of the distal and proximal end portions of the plurality of laminoplasty plates to allow fusion of the lamina portion in the relief position. In this example, the graft can be configured to surround at least a portion of the medial portion of the laminoplasty plates. In a specific example, the medial portion of the laminoplasty plate can be of reduced cross-sectional area relative to the distal and proximal end portions, and the graft can be substantially U-shaped to substantially surround the medial portion of the laminoplasty plate. Further, the graft can be composed of autologous bone, allograft bone, synthetic bone substitute, and osteoinductive agent.

In yet another aspect, the system for performing laminoplasty comprises a portal through which the methods provided herein can be performed. A standard portal can be used as long as the lamina setting tool can be operated from within the geometry of the portal. One issue that may arise in the use of a standard portal is the introduction of tissue into the portal when the first lamina portion is raised to its relief position. If the distal end of the standard portal is positioned onto a portion of the first lamina portion, it will elevate therewith. As such, in another aspect, the system comprises a laminoplasty portal 600.

In one exemplified aspect, the laminoplasty portal 600 comprises a substantially enclosed conduit defining an interior channel 610 and a circumferential sidewall 620. In one aspect, the circumferential sidewall comprises a first sidewall section 622 and an opposed second sidewall section 624, where the first sidewall section 622 and second sidewall section 624 are configured to slide longitudinally with respect to one another. In this fashion, in a first position, the distal ends of the two sidewall sections 632, 634 are substantially coextensive and are positioned substantially against the first and second lamina portions 210, 215. By coextensive, it is meant that the distal ends of the first and second sidewalls, in the first position, extend about the same amount such that they lie in a plane that is substantially transverse to the longitudinal axis of the interior channel. As the first lamina portion 210 is raised, the distal end 632 of the first sidewall section 622 raises along with it to a second position, leaving the distal end 634 of the second sidewall section 624 substantially adjacent the second lamina portion 215 and displaced from the distal end of the first sidewall section.

It is contemplated that the first sidewall section 622 and the second sidewall section 624 each comprise half of the tubular sidewall. It is also contemplated that the cross-section of the first sidewall section comprises a minor arc and the cross-section of the second sidewall section comprises a complimentary major arc, or vice-versa. It is also contemplated that the laminoplasty portal comprises a tubular shape other than cylindrical. In yet another aspect, the second sidewall section may comprise a leg 670 or other means by which to affix the laminoplasty portal to a fixed structure, such as a surgical table. It is contemplated that the tube may be of a different cross-sectional shape other than generally circular, such as square, elliptical, ovoid, polygonal, rectangular, etc.

In another aspect, the proximal end 640 of the portal is circumferentially integral and integral with the first sidewall section. In this aspect, the proximal end 644 of the second sidewall section 624 can be substantially adjacent a portion of the proximal end 642 of the first sidewall section 622 in the first position. In the second position, the proximal end 644 of the second sidewall section 624 can be spaced therefrom the proximal end 642 of the first sidewall section 622.

There are several means contemplated for permitting the two sidewall sections to longitudinally slide with respect to one another. The side edges of the two sidewalls can mate in several known fashions. In one aspect, one of the first or second sidewall sections comprises at least one longitudinal slot 650, while the other of the first or second sidewall sections comprises a complimentary longitudinal ridge 660 that is that fits within and slides with respect to the respective longitudinal slot. In another aspect, the longitudinal ridge is longitudinally shorter than the respective slot such that the ridge itself acts as a stop when the first sidewall has been slid with respect to the second sidewall a predetermined distance.

In an exemplified aspect, the distal ends of the first and second sidewall sections can be shaped to substantially conform to the first and second lamina portions. In one aspect, the distal end of the first sidewall section is angled to substantially mate with the first lamina portion.

It is also anticipated that a surgical access portal system, such as the laminoplasty portal, may be useful in other procedures in which the benefit of having two or more sliding portions of a tube system will aid in the efficient exclusion of tissue from the interior of the tube. As such, it is contemplated that the surgical access portal comprises three or more sliding sidewall sections in order to adjust to the geometry of the anatomical region in which the portal is used. Additionally, it is anticipated that a tube may optionally be secured to the area of interest in the procedure by a stabilizing arm or other element on the tube system that can be connected to the operating table through an intermediate connection and/or attached to the desired vertebra or bone via one or more attachment members, such as a threaded post into a stable portion of the bone.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings.

It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A method of treating cervical stenosis in a patient by relieving spinal cord compression, the method comprising:
   providing a lamina setting tool for raising a separated lamina portion to a relief position;
   providing a laminoplasty portal comprising a sidewall defining and substantially enclosing an interior channel, the sidewall comprising a first sidewall section having a proximal end and a distal end, and an opposed second sidewall section having a proximal end and a distal end, wherein the first sidewall section is slidingly engaged with the second sidewall section along the longitudinal length of the first sidewall section such that the first sidewall section slides longitudinally with respect to the second sidewall section while remaining longitudinally connected to a portion of the second sidewall section, wherein the first sidewall section is configured to move from a first position where the distal ends of the first and second sidewall sections are substantially coextensive, to a second position, where the distal end of the first sidewall section is raised with respect to the distal end of the second sidewall section;
   exposing at least a portion of a posterior side of a desired cervical vertebra of the patient, the cervical vertebra having a midline;
   positioning the distal ends of the first and second sidewall sections substantially against a portion of the cervical vertebra;
   inserting at least a portion of the lamina setting tool into the interior channel of the laminoplasty portal and affixing a portion of the lamina setting tool to the lamina portion and affixing a portion of the lamina setting tool to a portion of a lateral mass;
   making a partial first sagittal division in the posterior side of the desired cervical vertebra on a first side of the midline at a junction between the lamina portion and the lateral mass portion by directing a cutting tool through the interior channel of the laminoplasty portal and to the lamina portion;
   providing at least one laminoplasty plate;
   securing a first portion of the at least one laminoplasty plate to the lateral mass portion adjacent the partial first sagittal division;
   separating the lamina portion by completing the first sagittal division;
   raising the lamina portion to the relief position mechanically with the lamina setting tool while maintaining the connection with the lamina portion and the lateral mass portion with the lamina setting tool;
   securing a second portion of the at least one laminoplasty plate to a portion of the lamina portion in the relief position; and
   removing the lamina setting tool and the laminoplasty portal.

2. The method of claim 1, wherein the distal end of the first sidewall section is raised with respect to the distal end of the second sidewall section when the lamina setting tool raises the separated lamina portion to the relief position.

3. The method of claim 1, wherein the distal end of the first sidewall section is configured to abut the lamina portion, and wherein the distal end of the second sidewall section is configured to abut the lateral mass portion.

4. The method of claim 1, wherein a proximal end of the laminoplasty portal is circumferentially integral and integral with the proximal end of the first sidewall section.

5. The method of claim 1, wherein the distal ends of the first and second sidewall sections are shaped to substantially conform to an area substantially near the lamina portion and the lateral mass portion.

6. The method of claim 5, wherein the distal end of the first sidewall section is angled to substantially mate with the lamina portion.

7. The method of claim 1, wherein one of the first and second sidewall sections comprises at least one longitudinal slot and the other of the first and second sidewall sections comprises a complementary longitudinal ridge that fits within and slides with respect to a respective one of the at least one longitudinal slot, and wherein the complementary longitudinal ridge is longitudinally shorter than the respective one of the at least one longitudinal slot such that the complementary longitudinal ridge acts as a stop when the first sidewall section slides longitudinally a predetermined distance with respect to the second sidewall section.

8. The method of claim 7, wherein the complementary longitudinal ridge of the laminoplasty portal acts as a stop when the first sidewall section slides in a first longitudinal direction a predetermined distance with respect to the second sidewall section and in a second longitudinal direction that is opposed to the first longitudinal direction.

9. The method of claim 1, wherein the second sidewall section of the laminoplasty portal comprises a leg configured to affix the laminoplasty portal to a fixed structure.

10. The method of claim 9, wherein the fixed structure is a surgical table.

* * * * *